United States Patent
Mayotte

(10) Patent No.: US 8,126,553 B2
(45) Date of Patent: Feb. 28, 2012

(54) SENSING INTEGRITY DETERMINATION BASED ON CARDIOVASCULAR PRESSURE

(75) Inventor: Mark J. Mayotte, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 881 days.

(21) Appl. No.: 12/180,161

(22) Filed: Jul. 25, 2008

(65) Prior Publication Data

US 2009/0299429 A1   Dec. 3, 2009

Related U.S. Application Data

(60) Provisional application No. 61/058,093, filed on Jun. 2, 2008.

(51) Int. Cl.
*A61N 1/08* (2006.01)
(52) U.S. Cl. ............... 607/18; 607/14; 607/23
(58) Field of Classification Search ............ None
See application file for complete search history.

(56) References Cited

U.S. PATENT DOCUMENTS

| | | | |
|---|---|---|---|
| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,129,394 A | 7/1992 | Mehra |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,201,865 A | 4/1993 | Kuehn |

(Continued)

FOREIGN PATENT DOCUMENTS

EP     0488512 A2   6/1992

(Continued)

OTHER PUBLICATIONS

Reply to Written Opinion from corresponding PCT Application Serial No. PCT/US2008/009029 filed Aug. 28, 2009 (13 pages).

(Continued)

*Primary Examiner* — Carl H Layno
*Assistant Examiner* — Paula J Stice
(74) *Attorney, Agent, or Firm* — Stephen W. Bauer; Michael J. Ostrom

(57) ABSTRACT

Electrical noise may be discriminated from sensed heart signals based on cardiovascular pressure. A plurality of detected cardiovascular pressure values are respectively associated with a plurality of detected tachyarrhythmia events. In some examples, a variance in the cardiovascular pressure, e.g., above a threshold range, may indicate that the detected tachyarrhythmia events are at least partially attributable to electrical noise. In some examples, stimulation therapy to a heart of a patient may be controlled based on the detection of a tachyarrhythmia episode and a variability in the cardiovascular pressure values that are associated with the tachyarrhythmia episode. In other examples, a sensing integrity indication may be generated upon determining that a tachyarrhythmia episode was associated with a variable cardiovascular pressure.

34 Claims, 15 Drawing Sheets

U.S. PATENT DOCUMENTS

| | | |
|---|---|---|
| 5,215,081 A | 6/1993 | Ostroff |
| 5,224,475 A | 7/1993 | Berg et al. |
| 5,226,415 A | 7/1993 | Girodo et al. |
| 5,292,343 A | 3/1994 | Blanchette et al. |
| 5,312,441 A | 5/1994 | Mader et al. |
| 5,314,450 A | 5/1994 | Thompson |
| 5,324,315 A | 6/1994 | Grevious |
| 5,354,319 A | 10/1994 | Wyborny et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,507,746 A | 4/1996 | Lin |
| 5,507,786 A | 4/1996 | Morgan et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,660,183 A | 8/1997 | Chiang et al. |
| 5,707,398 A | 1/1998 | Lu |
| 5,722,997 A | 3/1998 | Nedungadi et al. |
| 5,730,141 A | 3/1998 | Fain et al. |
| 5,741,311 A | 4/1998 | Mc Venes et al. |
| 5,755,735 A | 5/1998 | Richter et al. |
| 5,755,736 A | 5/1998 | Gillberg et al. |
| 5,755,742 A | 5/1998 | Schuelke et al. |
| 5,776,168 A | 7/1998 | Gunderson |
| 5,814,088 A | 9/1998 | Paul et al. |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,910,156 A | 6/1999 | Cinbis et al. |
| 5,944,746 A | 8/1999 | Kroll |
| 6,067,473 A | 5/2000 | Greeninger et al. |
| 6,070,097 A | 5/2000 | Kreger et al. |
| 6,085,118 A | 7/2000 | Hirschberg et al. |
| 6,112,119 A | 8/2000 | Schuelke et al. |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,266,554 B1 | 7/2001 | Hsu et al. |
| 6,317,632 B1 | 11/2001 | Krig et al. |
| 6,317,633 B1 | 11/2001 | Jorgenson et al. |
| 6,434,428 B1 | 8/2002 | Sloman et al. |
| 6,445,952 B1 | 9/2002 | Manrodt et al. |
| 6,477,417 B1 | 11/2002 | Levine |
| 6,493,586 B1 | 12/2002 | Stahmann et al. |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,721,600 B2 | 4/2004 | Jorgenson et al. |
| 6,760,624 B2 | 7/2004 | Anderson et al. |
| 6,788,971 B1 | 9/2004 | Sloman et al. |
| 6,865,141 B2 | 3/2005 | Tada et al. |
| 7,047,083 B2 | 5/2006 | Gunderson et al. |
| 7,058,450 B2 | 6/2006 | Struble et al. |
| 7,167,747 B2 | 1/2007 | Gunderson et al. |
| 7,236,828 B2 | 6/2007 | Casavant et al. |
| 7,266,409 B2 | 9/2007 | Gunderson |
| 7,289,851 B2 | 10/2007 | Gunderson et al. |
| 7,333,855 B2 | 2/2008 | Gunderson et al. |
| 7,369,893 B2 | 5/2008 | Gunderson |
| 7,881,790 B1 * | 2/2011 | Turcott .......................... 607/17 |
| 2001/0031997 A1 | 10/2001 | Lee |
| 2001/0037366 A1 | 11/2001 | Webb et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0074026 A1 | 4/2003 | Thompson et al. |
| 2003/0204215 A1 | 10/2003 | Gunderson et al. |
| 2004/0015197 A1 | 1/2004 | Gunderson |
| 2004/0088018 A1 | 5/2004 | Sawchuk et al. |
| 2004/0106955 A1 | 6/2004 | Swerdlow et al. |
| 2004/0122487 A1 | 6/2004 | Hatlestad et al. |
| 2004/0186388 A1 | 9/2004 | Gerasimov |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0137636 A1 | 6/2005 | Gunderson et al. |
| 2005/0154421 A1 | 7/2005 | Ousdigian |
| 2005/0159785 A1 | 7/2005 | Rueter |
| 2005/0288725 A1 | 12/2005 | Hettrick et al. |
| 2006/0074454 A1 | 4/2006 | Freeberg |
| 2006/0235476 A1 | 10/2006 | Gunderson et al. |
| 2007/0282379 A1 | 12/2007 | Limousin et al. |
| 2008/0082012 A1 | 4/2008 | Gunderson et al. |
| 2008/0161872 A1 | 7/2008 | Gunderson |
| 2010/0198285 A1 * | 8/2010 | Rom ................................ 607/5 |

FOREIGN PATENT DOCUMENTS

| | | |
|---|---|---|
| EP | 1145737 A | 10/2001 |
| EP | 1269911 A2 | 1/2003 |
| EP | 1709993 A1 | 10/2006 |

OTHER PUBLICATIONS

International Search Report and Written Opinion from corresponding PCT Application Serial No. PCT/US2008/009029 mailed May 28, 2009 (18 pages).

Johnson, et al, "Acute Clinical Feasibility of an Integrated Pressure Sensor Defibrillation Lead Design" North American Society of Pacing and Electro-Physiology, May 2006 (1 page).

Stiles, Steve "Implanted LA-Pressure Sensor for Guiding HF-Therapy Promising in Trial Run" Heartwire, Medscape 2007 (3 pages).

International Preliminary Report on Patentability for PCT Application No. PCT/US2008/009029, mail date May 26, 2010, (9 pp).

Olson, W.H. et al. "Automatic Detection of Ventricular Fibrillation with Chronically Implanted Pressure Sensors," Journal of the American College of Cardiology, vol. 7, No. 2, Suppl. A, p. 182A, 35th Annual Scientific Session of the American College of Cardiology, Atlanta, GA., USA, Feb. 1986 (2 pgs.).

Invitation to Pay Additional Fees and, Where Applicable, Protest Fee from corresponding PCT Application Serial No. PCT/US2008/009029 mailed Feb. 20, 2009 (5 pgs.).

\* cited by examiner

| Interval | Systolic Pressure | Diastolic Presssure | Pulse Pressure | Max dp/dt | Min dp/dt |
|---|---|---|---|---|---|
| 142A/143A | 40 | 10 | 30 | 3 | -3 |
| 142B/143B | 40 | 10 | 30 | 3 | -3 |
| G | 40 | 10 | 30 | 3 | 0 |
| H | 40 | 39 | 1 | 0 | -1 |
| I | 39 | 16 | 23 | -0.5 | -3 |
| J | 16 | 10 | 6 | 0.3 | 0 |
| 142D/143D | 40 | 10 | 30 | 3 | -3 |
| K | 36 | 10 | 26 | 3 | 0 |
| L | 40 | 38 | 2 | 0.3 | 0 |
| M | 40 | 30 | 10 | 0 | -3 |
| N | 30 | 10 | 20 | 0 | -3 |
| O | 18 | 10 | 8 | 0.3 | -0.01 |

FIG. 7B

SENSING INTEGRITY DETERMINATION BASED ON CARDIOVASCULAR PRESSURE

This application claims the benefit of U.S. Provisional Application No. 61/058,093, entitled, "SENSING INTEGRITY DETERMINATION BASED ON CARDIOVASCULAR PRESSURE," and filed on Jun. 2, 2008, the entire content of which is incorporated herein by reference.

TECHNICAL FIELD

The disclosure relates to implantable medical devices, and, more particularly, to monitoring integrity of components associated with implantable medical devices.

BACKGROUND

A wide variety of implantable medical devices for delivering a therapy or monitoring a physiologic condition have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing. For example, electrodes or sensors may be located at a distal portion of the lead. A proximal portion of the lead may be coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals such as pulses or shocks for pacing, cardioversion or defibrillation pulses via electrodes of one or more implantable leads. In some cases, such an implantable medical device may sense for intrinsic depolarizations of the heart, and control the delivery of such signals to the heart based on the sensing. When an abnormal rhythm is detected, such as bradycardia, tachycardia or fibrillation, an appropriate electrical signal or signals (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation electrical signals to a patient's heart upon detecting ventricular fibrillation.

SUMMARY

In general, the disclosure is directed to techniques for discriminating electrical noise from sensed heart signals based on cardiovascular pressure. The pressure may be sensed at any suitable location within the heart, such as within the right atrium, right ventricle, left atrium or the left ventricle, or outside the heart, such as within a blood vessel. The sensed pressure varies based on the mechanical contraction and relaxation of the heart and, in some cases, the flow of blood within the heart or out of the heart associated with such mechanical contraction. The sensed pressure may be, for example, a systolic pressure, diastolic pressure, a pulse pressure, a maximum and minimum derivative of sensed pressure (s), or any combination thereof.

Cardiovascular pressure may be relatively regular during a tachyarrhythmia episode, such as a ventricular tachycardia episode, a ventricular fibrillation episode or a non-sustained tachyarrhythmia (NST) episode. In this way, the pressure may be used to determine the integrity of the tachyarrhythmia episode sensing. Although the mean pressure during tachyarrhythmia may change relative to the mean pressure during sinus rhythm, in some examples, cardiovascular pressure may exhibit relatively low peak-to-peak variability during a tachyarrhythmia episode, which may be similar to the variability during sinus rhythm. A tachyarrhythmia episode may be characterized by the presence of a threshold number of tachyarrhythmia events, which may be a heart cycle (or a "cardiac cycle") having a duration less than or equal a threshold duration. A regular pressure may be indicated by, for example, a low variance in cardiovascular pressure values that are associated with tachyarrhythmia events (e.g., which may reflect sensed heart depolarizations) of the tachyarrhythmia episode. Accordingly, during a tachyarrhythmia episode or during normal contraction of the heart (in the absence of an arrhythmia), measured pressure associated with the tachyarrhythmia events or regular sinus rhythms may have a relatively low variance, e.g., within a particular threshold percentage of a mean, median, maximum, minimum, or another threshold pressure value or successive heart cycles may be associated with pressure values in a particular range.

A relatively high variance in the measured or calculated pressure associated with a detected tachyarrhythmia episode may indicate that the detected tachyarrhythmia episode was a false positive, which may be attributable to electrical noise. The electrical noise may be at least partially generated by a lead-related condition, such as a change in the structure of the lead (e.g., a fractured conductor, loose set-screw, or a change in the electrical insulation), or electromagnetic interference. The electrical noise may not be synchronized with the heart contractions, and, therefore, may not be associated with a regular pressure cycle. Accordingly, if electrical noise is characterized as a heart signal, the sensed (or measured) pressure associated with the detected heart depolarizations may not match up with a regular pressure cycle. The measured pressures associated with each tachyarrhythmia event that is detected based on the mischaracterized electrical noise may have a greater variation compared to the true or appropriately measured pressures that correspond to true heart cycles.

Cardiovascular pressure variance may be used to confirm whether a detected tachyarrhythmia episode is a true episode or a false positive detection of a tachyarrhythmia episode. In some examples, stimulation to the patient's heart may be controlled based on a detection of a tachyarrhythmia episode and a cardiovascular pressure. For example, upon detecting a tachyarrhythmia episode, stimulation may be delivered only after determining that the pressure associated with the heart cycles used to detect the tachyarrhythmia episode are regular (e.g., have a low variance) and indicative of a sensed tachyarrhythmia. In this way, monitoring a pressure within the heart may be useful for detecting false positive tachyarrhythmia episodes and preventing unnecessary delivery of stimulation to the heart.

In other examples, heart pressure variance may be used to generate a sensing integrity alert or indication. For example, if a non-sustained tachyarrhythmia (NST) episode is detected, a medical device may determine whether the cardiovascular pressure values associated with the tachyarrhythmia events of the NST episode were regular, e.g., varied by less than a threshold percentage or value. A NST episode is a tachyarrhythmia episode in the sense that it may comprise, for example, a train of relatively short heart cycles (e.g., tachyarrhythmia events). However, the short cycles of a NST do not meet the requirements for triggering a therapeutic response. If the pressure was not regular, e.g., had a variability greater than a threshold value, the medical device may attribute the NST episode detection to electrical noise.

In some examples, a medical device delivering stimulation therapy to the heart of the patient may operate under a different mode or with different parameters and/or therapies upon generation of the sensing integrity alert or indication. In addition or instead, the sensing integrity alert or indication may be used to notify the patient and/or a clinician that medical attention is desirable.

In some examples, other aspects of the cardiovascular pressures associated with tachyarrhythmia events are considered instead of, or in addition to, variance for controlling delivery of stimulation, changing a stimulation or sensing mode, or generating an integrity alert. A mean or median of the associated pressure values may be considered, for example. As another example, a determination of whether a threshold number of the associated pressures are above or below a threshold may be considered.

In one aspect, the disclosure is directed to a method comprising detecting a tachyarrhythmia episode of a heart of a patient, where the tachyarrhythmia episode comprises a plurality of detected tachyarrhythmia events, analyzing a plurality of cardiovascular pressure values, each of the pressure values being associated with a respective one of the tachyarrhythmia events, and generating an indication based on the analysis of the plurality of pressure values.

In another aspect, the disclosure is directed to a system comprising a pressure sensor that monitors a pressure within a heart of a patient, and a processor that detects a tachyarrhythmia episode of the heart, wherein the tachyarrhythmia episode comprises a plurality of tachyarrhythmia events, analyzes a plurality of cardiovascular pressure values, each of the pressure values being associated with a respective one of the tachyarrhythmia events, and generates an indication based on the analysis of the plurality of pressure values.

In another aspect, the disclosure is directed to a system comprising means for detecting a tachyarrhythmia episode of a heart of a patient, where the tachyarrhythmia episode comprises a plurality of detected tachyarrhythmia events, means for analyzing a plurality of cardiovascular pressure values, each of the pressure values being associated with a respective one of the tachyarrhythmia events, and means for generating an indication based on the analysis of the plurality of pressure values In another aspect, the disclosure is directed to a computer-readable medium containing instructions. The instructions cause a programmable processor to detect a tachyarrhythmia episode of a heart of a patient, where the tachyarrhythmia episode comprises a plurality of detected tachyarrhythmia events, analyze a plurality of cardiovascular pressure values, each of the pressure values associated with a respective one of the tachyarrhythmia events, and generate an indication based on the analysis of the plurality of pressure values.

In another aspect, the disclosure is directed to a computer-readable medium containing instructions. The instructions cause a programmable processor to perform any whole or part of the techniques described herein.

BRIEF DESCRIPTION OF DRAWINGS

FIG. 7B is a table illustrating example pressure values.

DETAILED DESCRIPTION

Figure 1:
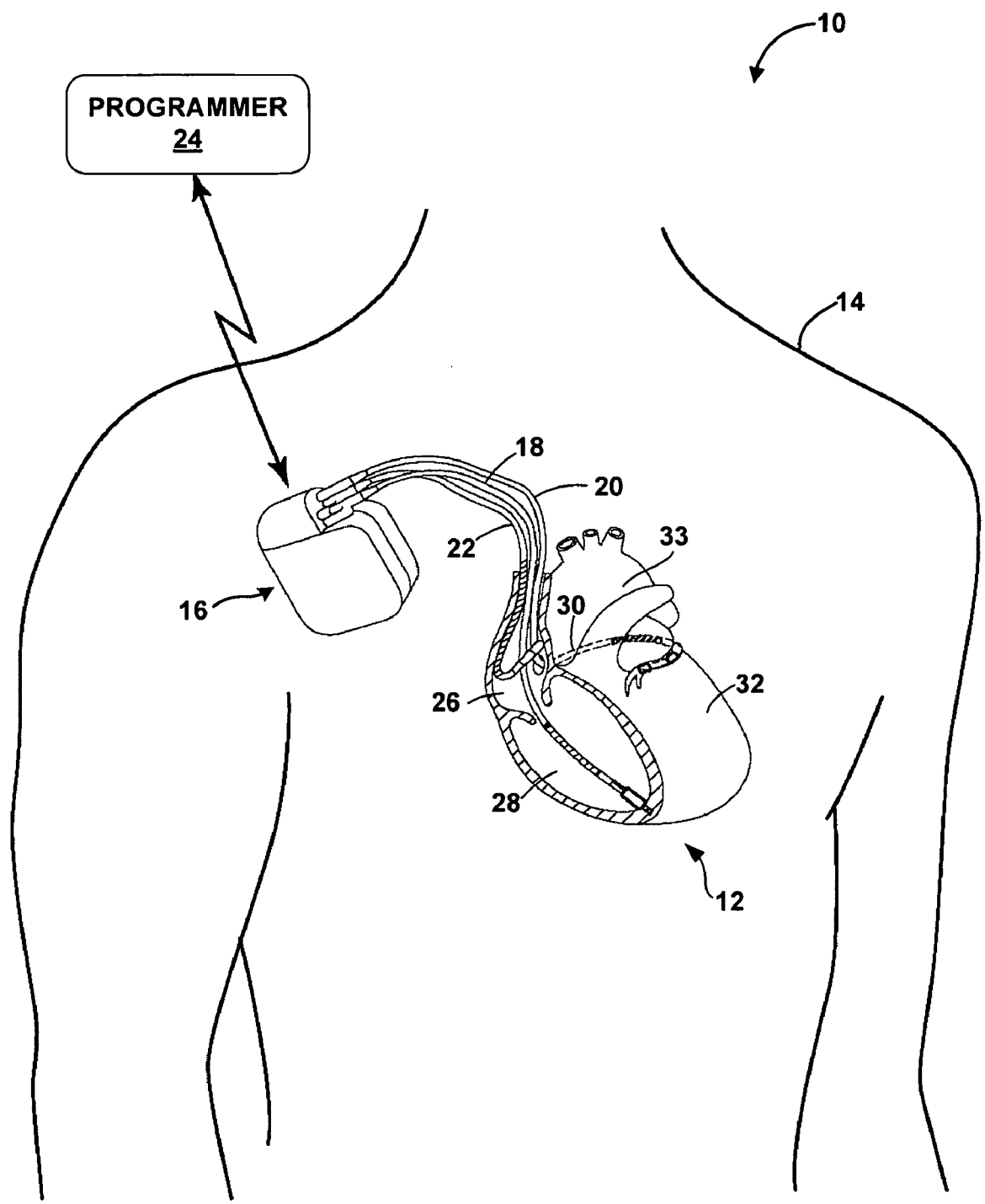
FIG. 1 is a conceptual diagram illustrating an example therapy system.

FIG. 1 is a conceptual diagram illustrating an example therapy system 10 that may be used to provide therapy to heart 12 of patient 14. Patient 12 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
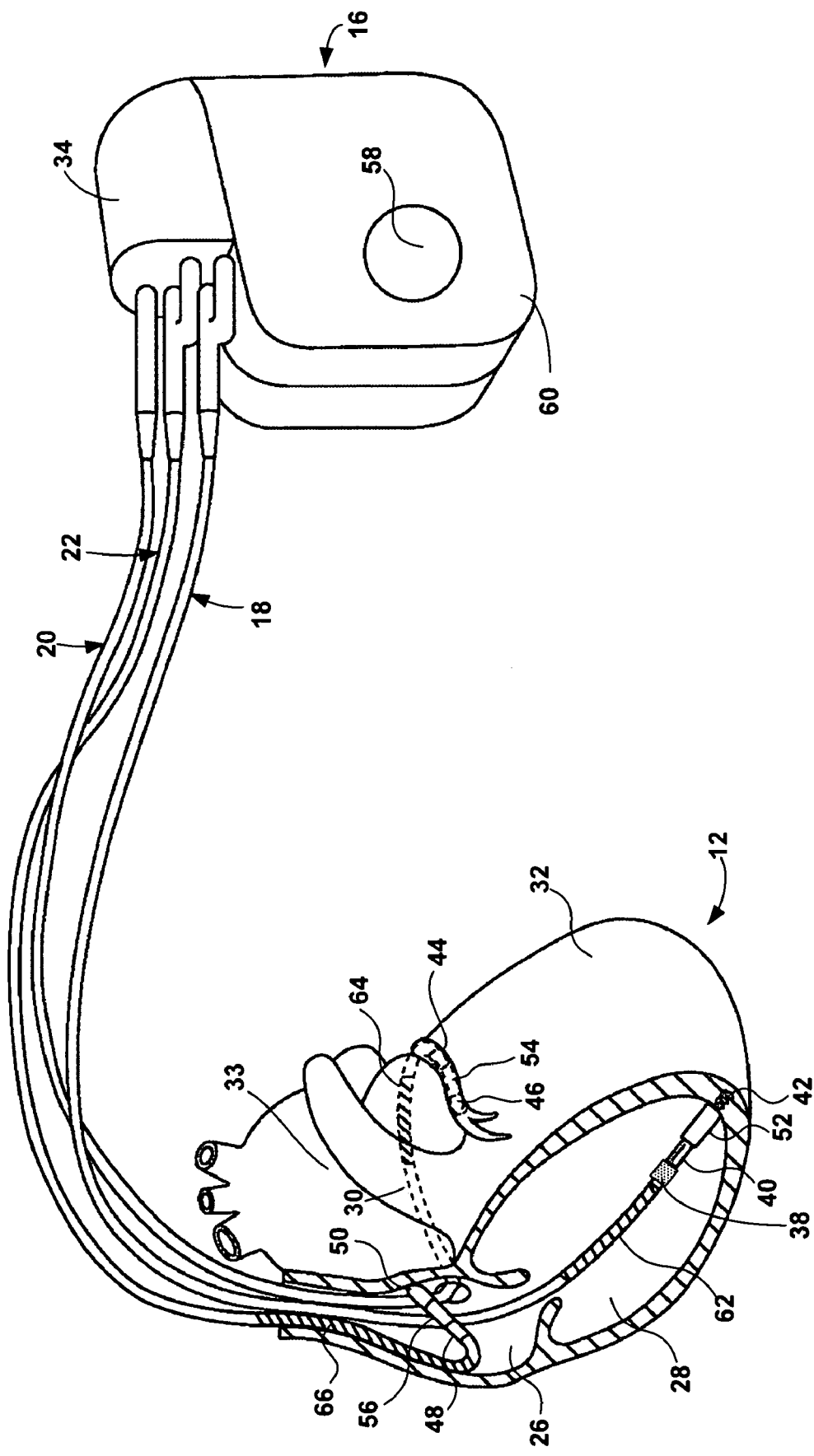
FIG. 2 is a conceptual diagram illustrating the medical device and leads of the therapy system of FIG. 1 in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 30 may respond to an absolute pressure inside right ventricle 28, and may be, for example, a capacitive or piezoelectric absolute pressure sensor. In other examples, pressure sensor 30 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As described in further detail with reference to FIG. 4, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes. In addition, in some examples, pressure sensor 38 may be self-contained device that is implanted within heart 12, such as within the septum separating right ventricle 28 from left ventricle 32, or the septum separating right atrium 26 from left atrium 33. In such an example, pressure sensor 38 may wirelessly communicate with IMD 16.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. As another example, other examples of therapy systems may include a single lead that extends from IMD 16 into right atrium 26 or right ventricle 28, or two leads that extend into a respective one of the right ventricle 26 and right atrium 28. An example of this type of therapy system is shown in FIG. 3.

Figure 3:
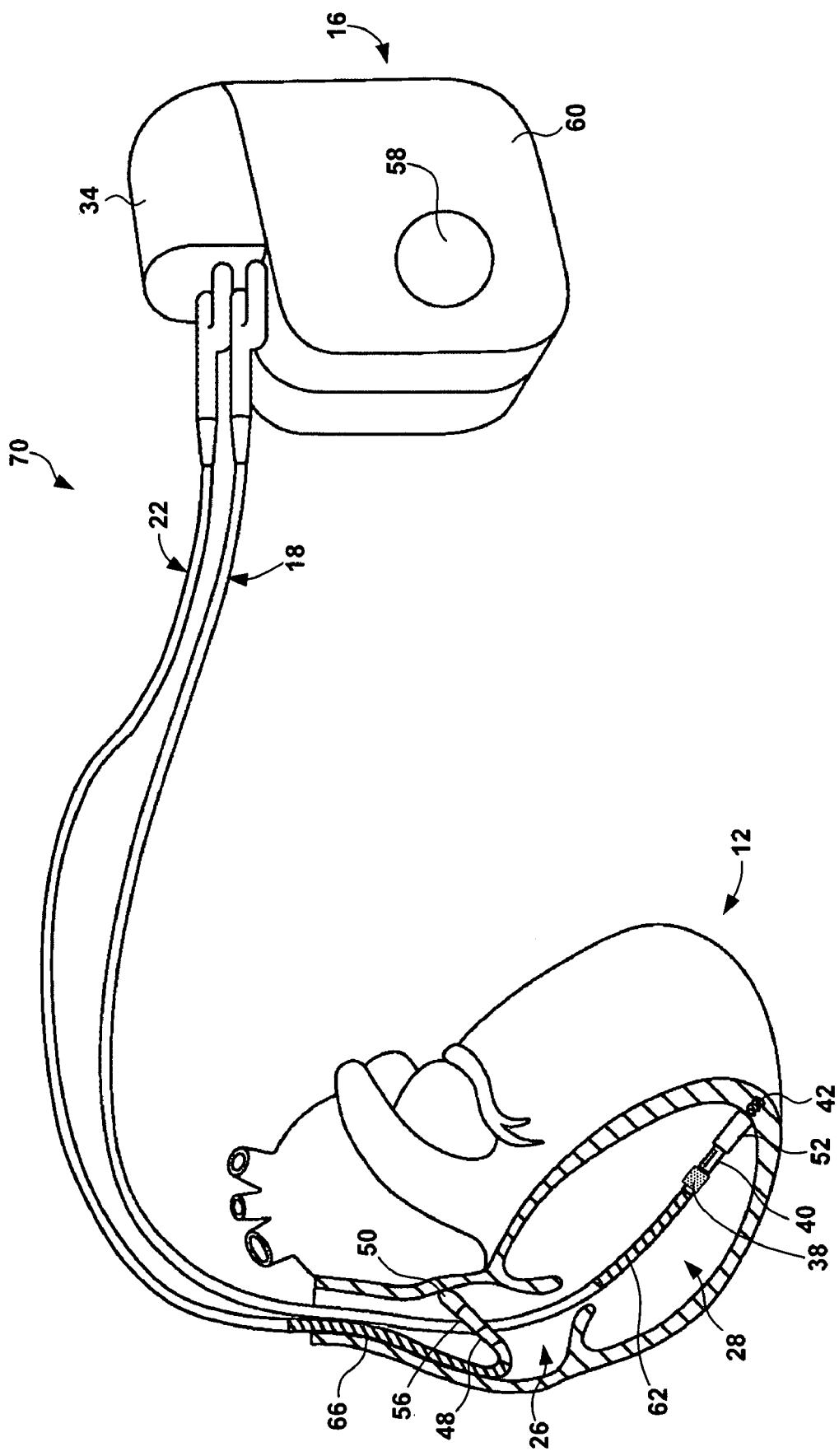
FIG. 3 is a conceptual diagram illustrating another example therapy system.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

Figure 4:
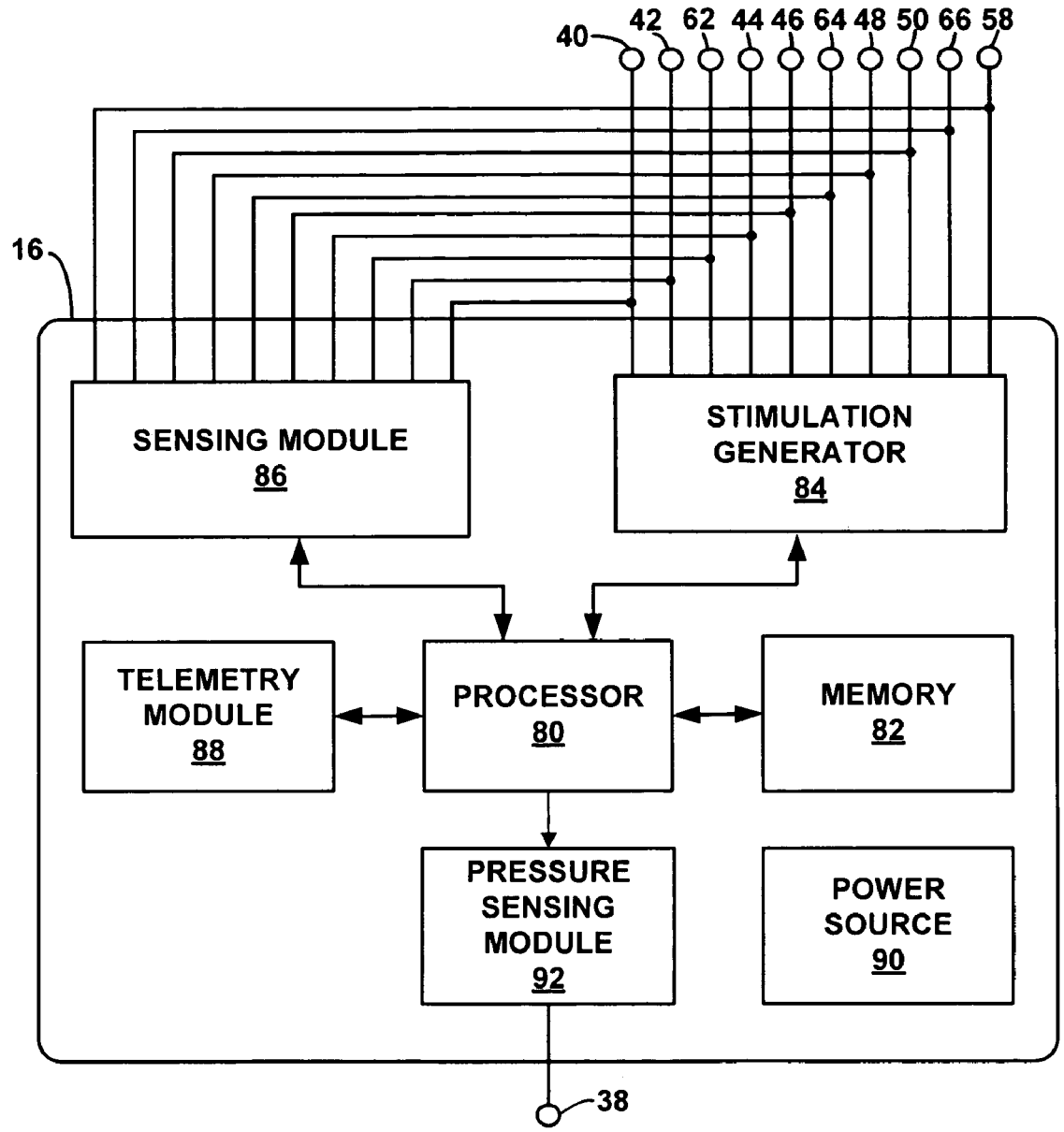
FIG. 4 is a functional block diagram of an example implantable medical device that delivers stimulation to a heart of a patient and measures a pressure within the heart.

FIG. 4 is a functional block diagram of one example configuration of IMD 16, which includes processor 80, memory 82, stimulation generator 84, sensing module 86, telemetry module 88, power source 90, and pressure sensing module 92. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy to heart 12. For example, stimulation generator 84 may deliver defibrillation shocks to heart 12 via at least two electrodes 58, 62, 64, 66. Stimulation generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, or a non-sustained tachycardia (NST) episode. As described in further detail below, processor 80 may, in some examples, deliver anti-tachyarrhythmia stimulation to heart 12 if the tachyarrhythmia events of the tachyarrhythmia episode are associated with relatively regular cardiovascular pressure values (which may be measured within heart 12 or otherwise within the cardiovascular system of patient 14), or if pressures associated with the episode are otherwise considered indicative of actual tachyarrhythmia. Examples of tachyarrhythmia episodes that may qualify for delivery of responsive therapy include a ventricular fibrillation episode or a ventricular tachyarrhythmia episode. In the case of a NST, however, processor 80 may not meet the requirements for triggering a therapeutic response, and, thus, processor 80 may continue normal operation if the pressures associated with the tachyarrhythmia episode are indicative of actual tachyarrhythmia.

In some examples, the pressure may be considered appropriate if the pressure variance between the tachyarrhythmia events is below a threshold percentage. As described in further detail below, pressure variance may refer to differences between pressure values associated with successive tachyarrhythmia events or differences between measured pressures and a mean or median of the measured pressures.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 80 in other examples.

In the examples described herein, processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 82 of IMD 16. In addition, the number of tachyarrhythmia events that are detected to confirm the presence of a tachyarrhythmia episode may be stored as a number of intervals to detect (NID) threshold value in memory 82. In some examples, processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 80 may determine that the tachyarrhythmia is present.

If processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation pulses to heart 12, stimulation generator 84 may include a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of stimulation generator 84.

Pressure sensing module 92 receives pressure signals from pressure sensor 38. Pressure sensor 38 may generate pressure signals itself or may modulate pressure signals conducted through lead 18. The pressure signals are a function of the fluid pressure at the site where pressure sensor 38 is disposed. In example shown in FIGS. 2 and 3, pressure sensor 38 is disposed in right ventricle 28 of heart 12. Pressure sensing module 92 may receive, monitor, and analyze the pressure signals, as will be described in more detail below. An example of a suitable pressure sensing module 92 includes the Chronicle Implantable Hemodynamic Monitor manufactured by Medtronic, Inc. of Minneapolis, Minn.

In some examples described below, processor 80 may receive a signal indicative of a cardiovascular pressure from pressure sensing module 92 and determine whether a detected tachyarrhythmia episode is a true episode or is based on detected electrical noise. For example, if the pressure values associated with tachyarrhythmia events (e.g., a heart cycle having a duration less than a threshold value) of the tachyarrhythmia episode are relatively regular, processor 80 may determine that the detected tachyarrhythmia episode was a true episode. In the examples described herein, a duration of a heart cycle (or a "cardiac cycle") may be measured between successive R or P waves, which in the case of fibrillation may be referred to as "fib" waves. This duration may also be referred to as an R-R or P-P interval. Although described below with reference to ventricular tachyarrhythmia, R-waves, and R-R intervals, the techniques described in this disclosure may also be applied in the context of detection of atrial tachyarrhythmia. As described below, based on this determination, processor 80 may control stimulation generator 84 to deliver therapy to heart 12.

On the other hand, if processor 80 determines that the pressure values associated with the tachyarrhythmia events of the tachyarrhythmia episode are not regular (e.g., vary by more than a threshold amount relative to each other or relative to a mean or median value of the pressure values associated with the tachyarrhythmia events), processor 80 may identify the detected tachyarrhythmia episode as an inappropriately detected episode. As described below, based on this determination, processor 80 may control stimulation generator 84 to withhold therapy and processor 80 may generate a sensing integrity alert. This alert may indicate to a patient or clinician that a review of the integrity of leads 18, 20, 22 is desirable or recommended.

Pressures sensing module 92, or, alternatively, processor 80, may measure, observe, or derive different pressure characteristics from the signals generated by pressure sensor 38. For example, in embodiments when pressure sensor 38 generates a signal indicative of the pressure within right ventricle 28, pressure sensing module 92 may measure the right ventricular systolic pressure by observing a peak pressure in right ventricle 28, and the right ventricular diastolic pressure may be measured by observing the pre-systolic low pressure in right ventricle 28. Pulse pressure may be the difference between the right ventricular systolic pressure and the right ventricular diastolic pressure.

Another pressure characteristic that pressure sensing module 92 may measure include the right ventricular mean pressure, which is the mean pressure in right ventricle 28 during a cardiac cycle. A cardiac cycle (or "heart cycle") typically includes at least a Q-wave, an R-wave, and an S-wave. Estimated pulmonary artery diastolic pressure (EPAD) is another pressure characteristic that may be indicative of activity within heart 12, which pressure sensing module 92 may monitor. EPAD reflects the pulmonary capillary wedge pressure, which reflects the average pressure in left atrium 33 over a cardiac cycle, which may also be referred to as the mean left atrial pressure. EPAD may also reflect the filling pressure in left ventricle 32 during diastole, also called the left ventricular end diastolic pressure. Techniques for measuring EPAD is described in U.S. Pat. No. 7,058,450 to Struble et al., entitled, "ORGANIZING DATA ACCORDING TO CARDIAC RHYTHM TYPE," which issued on Jun. 6, 2006 and is incorporated herein by reference in its entirety. Again, in various examples, pressure may be measured in other chambers of heart 12, or other locations within the cardiovascular system of patient 14, such as within a pulmonary artery.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac episodes that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

Although FIG. 4 illustrates pressure sensing module 92 as a separate component from processor 80, in other examples, processor 80 may include the functionality attributed to pressure sensing module 92 herein. For example, pressure sensing module 92 shown in FIG. 4 may include software executed by processor 80. If pressure sensing module 92 includes firmware or hardware, pressure sensing module 92 may be a separate one of the one or more processors 80 or may be a part of a multifunction processor. As previously described, processor 80 may comprise one or more processors.

Further, in other examples of therapy system 10, pressure sensing module 92 may be separate from IMD 16. That is, although pressure sensing module 92 is shown in FIG. 4 to be incorporated within housing 60 of IMD 16 along with other components such as processor 80, stimulation generator 84 and sensing module 86, in other examples, pressure sensing module 92 may be enclosed in a separate housing. The stand-alone pressure sensing module that is enclosed in a separate housing from IMD 16 housing 60 may be mechanically coupled to IMD 16 or may be mechanically decoupled from IMD 16. For example, in some examples, pressure sensing module 92 and pressure sensor 38 may be implanted within patient 14 at a separate location from IMD 16 and leads 18, 20, 22. Pressure sensing module 92 may communicate with IMD 16 via a wired connection or via wireless communication techniques, such as RF telemetry.

In yet other examples of therapy system 10, pressure sensing module 92 may be external to patient 14 and may receive signals from an implanted pressure sensor 38 via wireless telemetry. For example, programmer 24, which may be a patient programmer or a clinician programmer, may include pressure sensing module 92. As another example, a computing device other than programmer 24 may include pressure sensing module 92. In some examples, data from pressure sensor 38 and sensing module 86 may be uploaded to a remote server, from which a clinician or another user may access the data to determine whether a potential sensing integrity issue exists. An example of a remote server includes the CareLink Network, available from Medtronic, Inc. of Minneapolis, Minn. An example of a system that includes an external device, such as a server, and one or more computing devices that are coupled to IMD 16 and programmer 24 via a network is described below with respect to FIG. 13.

Further, in some examples, a pressure sensor may be external to patient 14 and sense the cardiovascular pressure of patient 14 externally. The external pressure sensor may communicate with IMD 16 via wireless communication techniques.

Figure 5:
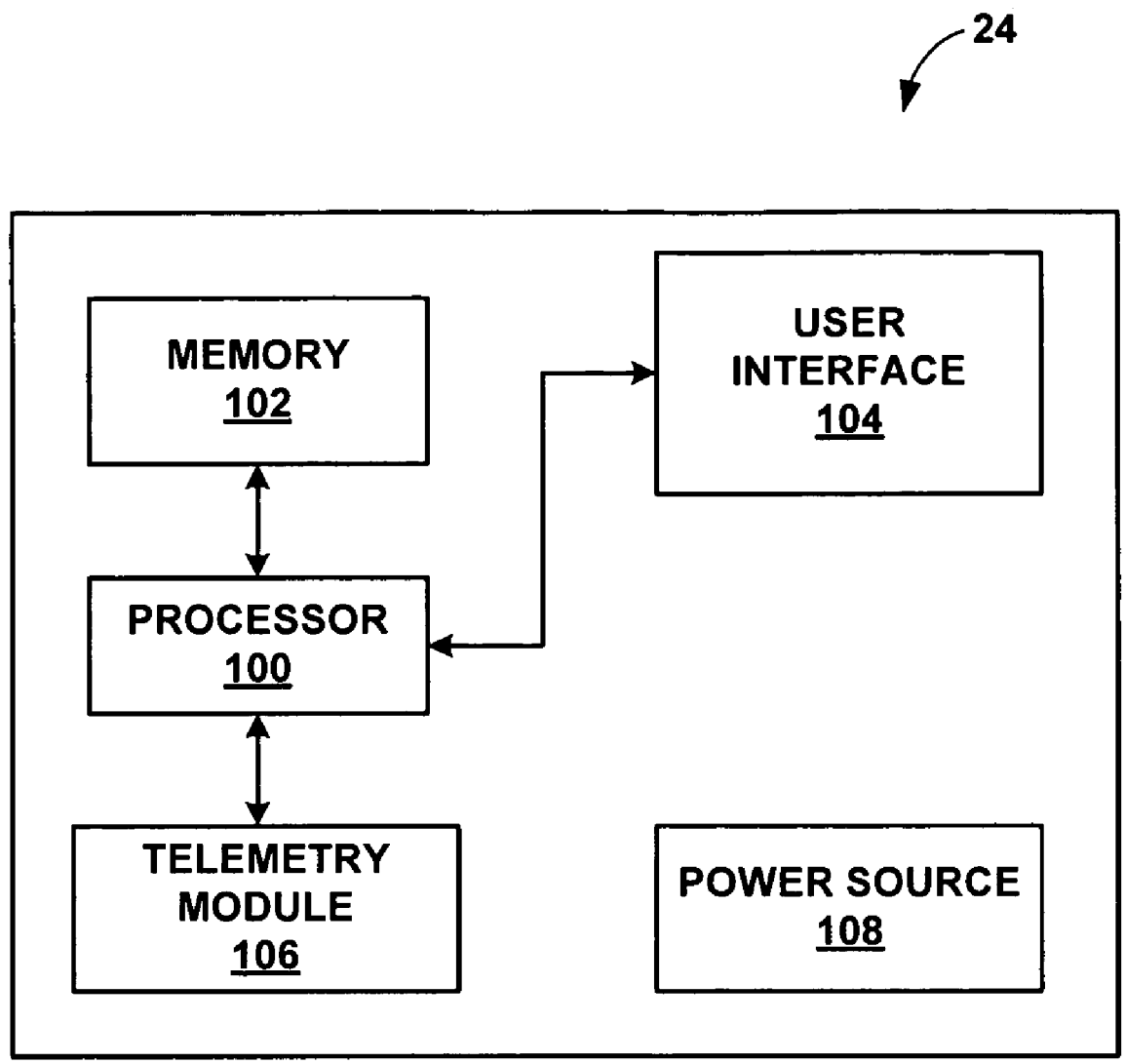
FIG. 5 is a functional block diagram of an example medical device programmer.

FIG. 5 is block diagram of an example programmer 24. As shown in FIG. 5, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 102 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 102 may be similar to telemetry module 88 of IMD 16 (FIG. 4).

Telemetry module 102 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Referring again to FIG. 4, processor 80 of IMD 16 may detect a tachyarrhythmia episode, such as a ventricular fibrillation, ventricular tachycardia, fast ventricular tachyarrhythmia episode, or a NST episode, based on electrocardiographic activity of heart 12 that is monitored via sensing module 86. For example, sensing module 86, with the aid of at least some of the electrodes 40, 42, 44, 46, 48, 50, 58, 62, 64, and 66 (shown in FIGS. 1-2), may generate an electrocardiogram (ECG) or electrogram (EGM) signal that indicates the electrocardiographic activity. Alternatively, sensing module 86 may be coupled to sense electrodes that are separate from the stimulation electrodes that deliver electrical stimulation to heart 12 (shown in FIGS. 1-3), and may be coupled to one or more different leads than leads 18, 20, 22 (shown in FIGS. 1-2). The ECG signal may be indicative of the depolarization of heart 12.

For example, as previously described, in some examples, processor 80 may identify the presence of a tachyarrhythmia episode by detecting a threshold number of tachyarrhythmia events (e.g., R-R or P-P intervals having a duration less than or equal to a threshold). In some examples, processor 80 may also identify the presence of the tachyarrhythmia episode by detecting a variable coupling interval between the R-waves of the heart signal.

In some cases, electrical noise may interfere with the ability of IMD 16 to accurately and precisely detect a tachyarrhythmia episode. For example, IMD 16 may sense electrical noise and interpret the electrical noise as an ECG/EGM signal. This may cause IMD 16 to oversense the heart rhythms, and, in some cases, erroneously detect a tachyarrhythmia event based on the electrical noise. For example, processor 80 of IMD 16 may interpret electrical noise as a heart rhythm, and detect the presence of a tachyarrhythmia episode or event (e.g., a heart cycle measured between successive R-waves that has a duration less than a threshold value) based on the electrical noise. Depending on the source of the electrical noise, the electrical noise may present itself as a relatively fast rhythm, which processor 80 may interpret as one or more tachyarrhythmia events, which may then be used to detect a tachyarrhythmia episode. As described above, in some examples, the IMD may detect the presence of a tachyarrhythmia episode by determining whether a certain number of intervals of a particular number of total intervals have a certain duration, e.g., whether a certain number of intervals are considered tachyarrhythmia events.

Oversensing of the heart rhythms may result in inappropriate withholding or delivery of electrical stimulation to heart 12. For example, oversensing may cause the IMD to detect a tachycardia or fibrillation episode when heart 12 is in a normal sinus rhythm, which may result in the inappropriate delivery of a high voltage shock therapy.

Electrical noise that IMD 16 characterizes as heart rhythms may be attributable to different sources. In some examples, electrical noise may be attributable to a lead-related condition, which may include, for example, a change in the structure of at least a part of the lead. For example, a conductor within the lead may fracture or electrical insulation of one of the conductors within the lead may change, thereby causing conductors to contact one another or with body fluids and resulting in a low impedance or a short circuit. In other cases, a lead conductor may fracture and exhibit an intermittent or continuous open circuit resulting in intermittent or continuous high impedance. The lead-related condition may occur during implantation of the lead or after implantation of lead, as stresses are applied to the lead during movement of patient 14 and/or from regular movement of heart 12.

As another example, a lead-related condition may occur when an electrical connection between IMD 16 and an electrical contact of a lead becomes intermittently or continuously disrupted. For example, set screws may loosen, which may result in the lead gradually loosening from IMD 16. The disruption of the connection between the electrical contact of a lead and the IMD may result in an open circuit or a high impedance circuit.

Pressure sensing module 92 of IMD 16 generates a signal indicative of a cardiovascular pressure, which may be used to discriminate electrical noise from heart signals (e.g., an EGM signal). As described above, in different embodiments, pressure sensing module 92 may monitor a pressure within right atrium 26, right ventricle 28, coronary sinus 30, left atrium 33, or other regions of heart 12. Instead or in addition to sensing a pressure within heart 12, pressure sensing module 92 may sense a pressure within the vasculature of patient 12, e.g., within a vein. Accordingly, while a pressure within right ventricle 28 is primarily referred to with reference to FIGS. 6-12, in other examples, pressure sensing module 92 may monitor a pressure within other portions of heart 12 or vasculature to help discriminate electrical noise from heart signals.

Figure 6A:
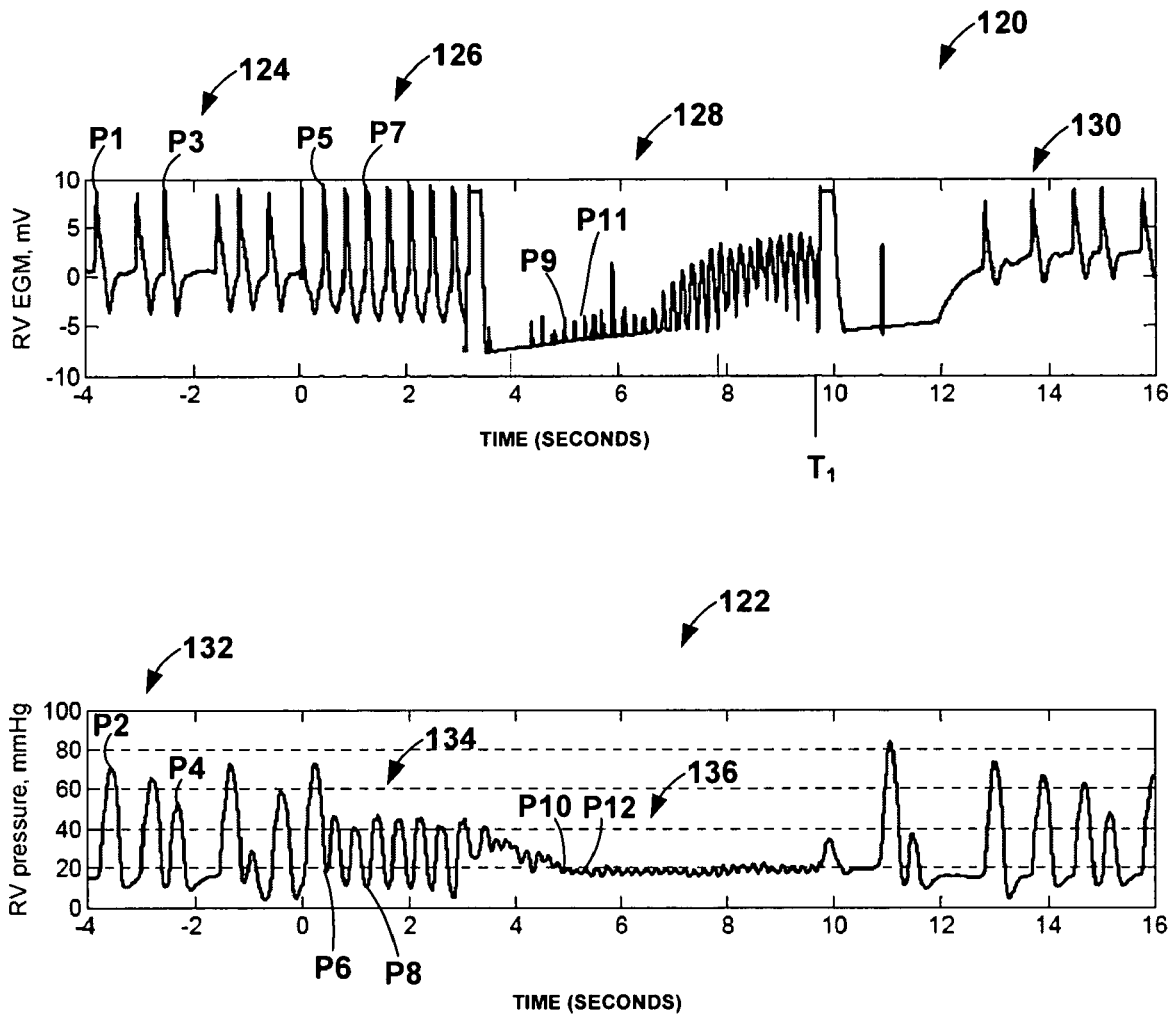
FIG. 6A illustrates an electrogram (EGM) that indicates electrical activity within a heart of a patient and a graph of pressure measurements within the heart.

FIG. 6A illustrates an electrogram (EGM) 120 that indicates electrical activity within right ventricle 28 of heart 12

(measured in millivolts), and a pressure graph 122 that indicates pressure measurements within right ventricle 28 (measured in millimeters of mercury (mmHg)) over time. EGM 120 and pressure graph 122 were generated using a heart of a human subject, and are shown to conceptually illustrate a relationship between cardiovascular pressure variance and tachyarrhythmia events.

A first portion 124 of EGM 120 indicates a regular heart rhythm (e.g., a regular sinus rhythm) that is characterized by heart cycles having a duration within a particular range of values. In some examples, the heart cycle may be measured between successive R-waves or P-waves. A second portion 126 of EGM 120, beginning at time "0," indicates a faster heart rhythm, which is indicative of the occurrence of heart cycles due to rapid ventricular pacing (which might be similar in nature to ventricular tachycardia events due to their duration) used to induce ventricular fibrillation during device testing. Thus, while second portion 126 does not reflect true ventricular tachycardia events, the heart cycles shown in portion 126 will be referred to as representative ventricular tachycardia events.

In FIG. 6A, the representative ventricular tachycardia events continue for about 3 seconds, at which time, the heart rhythm further shortens upon induction of ventricular fibrillation via a synchronized shock on the T-wave, indicating the occurrence of heart cycles having a particular duration that characterizes them as ventricular fibrillation events. The ventricular fibrillation events are shown in third portion 128 of EGM 122. At time T1, a defibrillation shock is delivered to heart 12 in order to return heart 12 to a normal rhythm, indicated by fourth portion 130 of EGM 120.

Pressure graph 122 illustrates pressure measurements within right ventricle 28 over time. The pressure changes within right ventricle 28 may correspond to the contraction of heart 12 and the flow of blood through heart 12. As heart 12 contracts and blood pumps through right ventricle 28 (or another region of heart 12 in which a pressure sensor measures pressure), the pressure within right ventricle 28 sensed by pressure sensing module 92 changes. Each heart cycle is associated with a pressure cycle that includes a diastolic pressure and a systolic pressure.

As pressure graph 122 indicates, a relatively regular measured pressure cycle may be associated with a heart rhythm during a normal sinus rhythm as well as during a tachyarrhythmia episode. For example, for each heart cycle in first portion 124 of EGM 120, a corresponding pressure cycle (i.e., a pressure cycle that generally corresponds in time with the heart rhythm) and a pressure cycle associated with the previous or successive heart rhythm have a relatively low variance. As another example, each heart cycle in first portion 124 of EGM 120 may be associated with a particular pressure value that varies by less than or equal to a threshold percentage relative to a mean or median of all of the pressure values of in the first portion 124 of EGM 120. Other statistical analyses to characterize the variability of the pressure values associated with the heart cycles are contemplated.

The pressure cycle that corresponds to the heart cycle generally corresponds in time with the heart cycle and has a surrogate systolic pressure and a surrogate diastolic pressure. The surrogate systolic pressure may be, for example, the maximum pressure in a predetermined pressure sensing window, which may be selected by a clinician. In some examples, the pressure sensing window may be selected to be equal to or less than an average duration between successive R-waves during the particular tachyarrhythmia episode. The pressure sensing window may begin at a predetermined point within the heart cycle, such as at the first R-wave if the heart cycle is measured between successive R-waves. A surrogate diastolic pressure may be, for example, the lowest pressure measurement during the predetermined pressure sensing window. Although R waves are used to describe the beginning of a pressure sensing time windows herein, in other examples, other portions of a heart wave (such as the P wave, Q wave, S wave or T wave) may be used to mark the beginning of a pressure sensing time window.

Regardless of the absolute pressure values during the normal heart rhythms 124, or the tachyarrhythmia events (at EGM portions 126, 128), the measured pressures within right ventricle 28 over time have a relatively low variance during the normal heart rhythm 124 and the tachyarrhythmia events. In some examples, a pressure variance may refer to a difference between the average pressure values, peak pressure values (e.g., a systolic pressure value), lowest pressure values (e.g., a diastolic pressure value), or pulse pressure values (a difference between the systolic and diastolic pressures) of two or more pressure cycles. The pressure cycles may or may not be "true" pressure cycles in the sense that the detection window for measuring a pressure cycle may change depending on whether the detected heart cycle associated with the sensed pressure cycle is based on a true heart cycle or based on electrical noise. In other examples, a pressure variance may refer to a difference between pressure values at a particular time (which may be arbitrarily selected by a clinician) during the pressure cycle of two or more successive pressure cycles. For example, processor 80 may compare pressure measurements at about 10 milliseconds (ms) into the pressure sensing time window for successive pressure cycles.

As another example, processor 80 may determine the cardiovascular pressure values associated with each of the detected tachyarrhythmia events are regular, e.g., have a low variance, if the pressure associated with at least one tachyarrhythmia event varies by no more than a threshold percentage compared to the average pressure of at least two or more prior tachyarrhythmia events. In some examples, pressure variance may refer to differences between measured pressure values and a mean or median of the measured pressure values of different sensed events. The differences may be absolute. In some examples, pressure variance may refer to a mean or median value of such differences.

For example, processor 80 may determine an absolute difference between each of the pressure values associated with the detected tachyarrhythmia events and a mean value or median value of the pressure values. If the absolute difference falls within to a threshold value or a threshold range, processor 80 may determine that the pressure variance was relatively low.

As another example, processor 80 may determine the variability in the pressure values by determining an absolute difference between each of the pressure values associated with the detected tachyarrhythmia events and a mean value or a median value of the pressure values, and determine a mean or median value of the absolute differences. If the mean or median value of the absolute differences is within a threshold range, e.g., about 5 percent (%) to about 25% of the mean value or a median value of the pressure values, processor 80 may determine that the pressure variance associated with the detected tachyarrhythmia events was relatively low. As previously discussed, a relatively low measured pressure variance may indicate that detected tachyarrhythmia events were true events, whereas a relatively high measured pressure variance may indicate that the detected tachyarrhythmia events were at least partially based on electrical noise.

In another example, processor 80 may determine whether detected tachyarrhythmia events are true events based on a derivative of the measured pressure values associated with the detected tachyarrhythmia events. That is, processor 80 may evaluate the change in pressure values over time to determine whether the measured pressure values indicate the detected tachyarrhythmia events were true events, e.g., based on actual heart signals. In some cases, each pressure waveform associated with a true heart cycle may have a positive slope and a negative slope in a particular pattern. For example, if the true heart cycle is measured between successive R-waves, the true pressure cycle associated with the true heart cycle may have a positive sloped followed by a negative slope. If processor 80 determines that the derivative of the measured pressure cycle associated with a detected tachyarrhythmia event does not have the predetermined pattern of the positive slope and negative slope of a true pressure cycle associated with a true heart cycle, processor 80 may determine that the detected tachyarrhythmia events were at least partially detected based on electrical noise.

The threshold at which the pressure variability is considered relatively low, e.g., relatively regular, may be selected by a clinician and, in some examples, may dynamically change based on the measured heart pressures for a particular patient. In some examples, processor 80 may determine that the variance in the heart pressure associated with the tachyarrhythmia events is relatively low if the pressure variability remains below a predetermined threshold percentage, such as about 5% to about 25%, e.g., about 10%. However, other threshold percentages are contemplated.

As an example of the relatively low variance in pressure associated with normal cardiac cycles 124, point P1 of EGM 120 indicates an R-wave of a heart rhythm, and point P2 of pressure graph 122 indicates the surrogate systolic pressure that correlates to the R wave at point P1. That is, point P2 indicates the surrogate systolic pressure that occurs within the predetermined pressure sensing window (i.e., during the pressure cycle) following the R-wave indicated by point P1. In the example shown in FIG. 6A, the predetermined pressure sensing window may be, for example, about 0.5 seconds to about 1 second, such as about 0.8 seconds. However, other pressure sensing time windows may be used and may be selected such that the pressure cycles for successive cardiac cycles substantially do not overlap. Point P3 of EGM 120 indicates an R-wave of a cardiac cycle that follows the cardiac cycle including the R-wave at point P1, and point P4 of pressure graph 122 indicates a surrogate systolic pressure during the pressure cycle that corresponds to the heart rhythm including the R-wave at point P3.

The regularity of the pressure within right ventricle 28 may be determined based on the pressure values at points P2 and P4. For example, if processor 80 determines that the surrogate systolic pressure values at points P2 and P4 are within a range of about 10%, then processor 80 may determine that the heart pressure within right ventricle 28 is relatively regular. In other examples, processor 80 may determine whether the pressure within right ventricle 28 is regular based on surrogate diastolic pressures, surrogate pulse pressures or other values, such as a pressure associated with an arbitrary point in time within the pressure sensing time window. Furthermore, more than two pressures may be compared for purposes of accessing variability, as described above.

When processor 80 detects a ventricular tachycardia episode, e.g., as indicated by the representative ventricular tachycardia events in portion 126 of EGM 120, processor 80 may determine whether the pressures associated with the ventricular tachycardia events of the ventricular tachycardia episode are regular. For example, point P5 of EGM 120 may be an R-wave of a heart cycle associated with a first representative ventricular tachycardia event (e.g., a heart cycle having a duration less than or equal to a ventricular tachycardia threshold value), and point P6 may be the surrogate diastolic pressure during the pressure cycle that corresponds to the first representative ventricular tachycardia event. Processor 80 may determine the surrogate diastolic pressure by determining a lowest pressure value during a pressure sensing time window that begins at the R-wave at point P5. In the example shown in FIG. 6A, the pressure sensing time window for determining the pressure of heart 12 during a ventricular tachycardia event may be about 0.25 seconds to about 0.5 seconds, such as about 0.4 seconds, although other time ranges are contemplated.

Point P7 of EGM 120 may be an R-wave of a second representative ventricular tachycardia event that immediately follows the heart cycle associated with the R-wave at point P5. Point P8 may be the surrogate diastolic pressure during the pressure cycle that corresponds to the second representative ventricular tachycardia event that includes the R-wave at point P7. Again, processor 80 may determine the surrogate diastolic pressure by determining a lowest pressure value during a pressure sensing time window that begins at the R-wave at point P7.

The regularity of the pressure within right ventricle 28 during associated with the first and second representative ventricular tachycardia events (which may or may not amount to a ventricular tachycardia episode) may be determined based on the surrogate diastolic pressure values at points P6 and P8, or the surrogate diastolic pressure values associated with more than two representative ventricular tachycardia events. For example, if processor 80 determines that the surrogate diastolic pressure values at points P6 and P8 are within a range of about 10%, then processor 80 may determine that the heart pressure within right ventricle 28 is relatively regular during the occurrence of the representative ventricular tachycardia events. In other examples, processor 80 may determine whether the pressure within right ventricle 28 is regular based on surrogate systolic pressures, surrogate pulse pressures or other values, such as an average pressure value within the pressure sensing time window.

Again, more than two pressures may be compared for purposes of accessing variability, as described above. For example, processor 80 may determine that the pressure associated with the ventricular tachycardia events is irregular if the difference between the pressure value at point P6 and/or P8 and the mean pressure value or median pressure value associated with two or more of the detected ventricular tachycardia events exceeds a threshold. Alternatively, processor 80 may determine whether the mean absolute difference between the pressure values associated with a respective one of two or more ventricular tachycardia events exceeds a threshold percentage relative to the mean pressure value.

When processor 80 of IMD 16 detects ventricular fibrillation events, e.g., as indicated by the heart rhythm in portion 128 of EGM 120, processor 80 may determine a variability of the pressure values associated with the ventricular fibrillation events. For example, point P9 of EGM 120 may be an R-wave of a heart cycle that indicates a first ventricular fibrillation event, and point P10 may be the surrogate pulse pressure during the pressure cycle that corresponds to the first ventricular fibrillation event. Processor 80 may determine the surrogate diastolic pressure by determining a lowest pressure value during a pressure sensing time window that begins at the R-wave at point P9. In the example shown in FIG. 6A, the pressure sensing time window for determining the pressure of heart 12 associated with a ventricular fibrillation event may be about 0.05 seconds to about 0.15 seconds, such as about 0.25 seconds, although other time ranges are contemplated.

Point P11 of EGM 120 may be an R-wave of a heart cycle during a second ventricular fibrillation event that immediately follows the first ventricular fibrillation event. Point P12 may be the surrogate pulse pressure during the pressure cycle that that corresponds to the second ventricular fibrillation event that includes the R-wave at point P11. Again, processor 80 may determine the surrogate diastolic pressure by determining a lowest pressure value during a pressure sensing time window that begins at the R-wave at point P11.

The regularity of the pressure within right ventricle 28 during the ventricular fibrillation events may be determined based on the surrogate diastolic pressure values at points P10 and P12. For example, if processor 80 determines that the surrogate diastolic pressure values at points P10 and P12 are within a range of about 10%, then processor 80 may determine that the pressure values within right ventricle 28 that are associated with the detected ventricular fibrillation events are relatively regular (e.g., has a low variability). In other examples, processor 80 may determine whether the pressure within right ventricle 28 is regular the ventricular fibrillation events based on surrogate systolic pressures, surrogate diastolic pressures or other values. Again, more than two pressures may be compared for purposes of accessing variability in some examples, as described above.

Figure 6B:
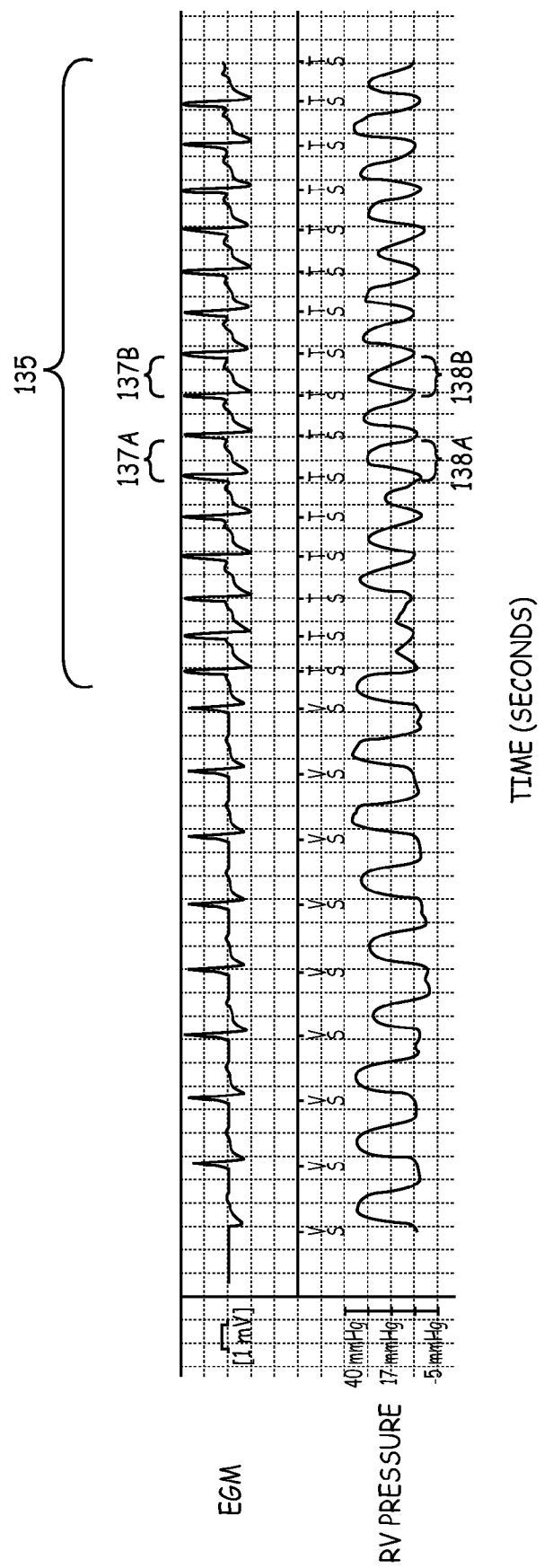
FIG. 6B illustrates an EGM that indicates a true ventricular tachycardia event of a patient.

FIG. 6B illustrates an EGM measured between a housing of an IMD and a coil electrode in a right ventricle of a human subject, whereby portion 138 illustrates a true ventricular tachycardia episode. In addition, FIG. 6B illustrates a graph that represents pressure values associated with the ventricular tachycardia events of the ventricular tachycardia episode. As shown in FIG. 6B, the true ventricular tachycardia events are associated with regular pressure values having low variability. Variability of the measured pressure values or derived pressure values may be determined using any of the techniques described above. For example, ventricular tachycardia event 137A is associated with pressure cycle 138A (e.g., corresponds in time to pressure cycle 138A) and ventricular tachycardia event 137B is associated with pressure cycle ventricular tachycardia event 138B. Each pressure cycle 138A, 138B may have a surrogate systolic, surrogate diastolic or a surrogate pulse pressure value that differs from a mean value of all of the pressure cycles that correspond in time to ventricular tachycardia episode 138 by less than a threshold value.

Figure 7A:
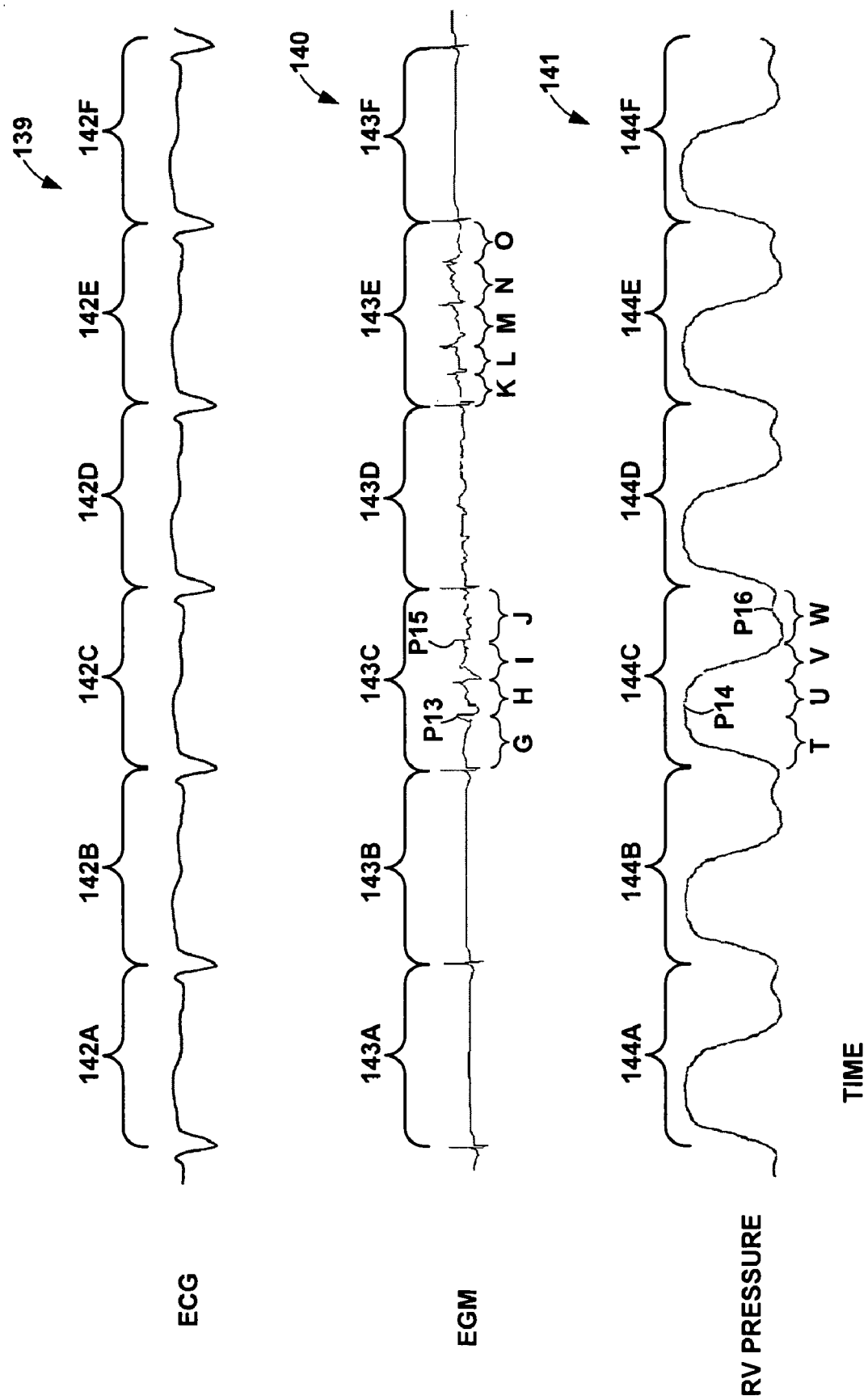
FIG. 7A illustrates a conceptual electrocardiogram, a conceptual electrogram with electrical noise, and a conceptual graph of measured pressure values over time.

FIG. 7A illustrates a conceptual ECG 139, EGM 140, and pressure graph 141 of pressure values measured in a right ventricle of heart 12. ECG 139 illustrates true heart cycles during a normal sinus rhythm in which tachyarrhythmia events are not occurring. For example, portions 142A-142F of ECG 139 and portions 143A-143F EGM 140 illustrate true heart cycles measured between successive R-waves. Heart cycles 142A-142F of ECG 139 generally correspond to heart cycles 143A-143F, respectively, of EGM 140. That is, heart cycles 142A-142F are the same heart cycles as 143A-143F, respectively, where ECG 139 illustrates heart signals sensed via external electrodes and EGM 140 illustrates heart signals sensed via implanted electrodes.

As shown in FIG. 7A, each heart cycle 142A-142F of ECG 139 and each heart cycle 143A-143F is associated with a relatively similar pressure cycle 144A-144F, respectively. The pressure cycles 144A-144F have systolic pressure values, diastolic pressure values, and pulse pressure values within a particular range of each other or within a particular percentage of a mean systolic value, mean diastolic pressure value or mean pulse pressure value of the pressure cycles 143A-143F. The different types of pressure values associated with the heart cycles 142A-142F (or 143A-143F) are shown in the table of FIG. 7B.

The conceptual EGM 140 illustrates electrical noise within portions 143C, 143D, and 143E. If processor 80 receives EGM 140 from sensing module 86, processor 80 may characterize the electrical noise as sensed heart rhythms. Accordingly, in some cases, processor 80 may determine whether a tachyarrhythmia episode is occurring based on the electrical noise, rather than a heart rhythm. For example, processor 80 may determine that portions G-N of EGM 140 is a heart rhythm that indicates ventricular tachycardia events due to, e.g., the short time interval of each noise cycle, which may be mistaken for a heart rhythm. Thus, instead of characterizing the true heart cycle 143C as such, sensing module 86 may provide a signal to processor 80 that indicates portions G-J are detected heart cycles within the same time frame as the true heart cycle 143C. Portions G-J of EGM 140 are measured between waves that appear to be R-waves, but are not true R-waves because the portions G-J represent electrical noise. Electrical noise may have successive short (e.g., less than about 140 ms) intervals. The duration of an interval (e.g., between successive R-waves or P-waves) that constitutes a "short" interval may be less than the duration of time required to characterize a heart cycle as a ventricular tachycardia event or a ventricular fibrillation event.

Similarly, sensing module 86 may provide a signal to processor 80 that indicates portions K-O are detected heart cycles within the same time frame as the true heart cycle 143E. Portions K-O of EGM 140 are measured between waves that appear to be R-waves, but are not true R-waves because the portions K-O are based on electrical noise.

As FIG. 7A illustrates, erroneously detected tachyarrhythmia events that are caused by electrical noise are not associated with relatively regular cardiovascular pressures. For example, processor 80 may characterize portion P of pressure graph 141 as a pressure cycle that is associated with the detected ventricular tachyarrhythmia event G. As shown in FIG. 7B, the measured pressure values of the pressure cycle P associated with detected ventricular tachyarrhythmia event G differ from the true pressure cycles 144A-144F that are associated with the true heart cycles 142A-142F and 143A-143F, respectively. Similarly, processor 80 may characterize portions U-W of pressure graph 141 as pressure cycles associated with the detected ventricular tachyarrhythmia events H-J, respectively.

As FIG. 7B illustrates, the ventricular tachyarrhythmia events H-O detected at least partially based on electrical noise may not be associated with relatively similar pressure values. Processor 80 may determine the pressure values (e.g., systolic, diastolic, and pulse pressure values) based on a pressure sensing window that begins at the characterized R-wave for the associated detected heart cycle. For example, processor 80 may characterize point P13 of EGM 140 as a first R-wave of the detected ventricular tachyarrhythmia event H. Processor 80 may determine the surrogate systolic pressure by determining a highest pressure value during a pressure sensing time window that begins at the characterized R-wave at point P13. In FIG. 7A, the surrogate systolic pressure for pressure cycle U associated with the detected tachyarrhythmia event H is at point P14. In the example shown in FIG. 7A, the pressure sensing time window for determining the pressure of heart 12 during a ventricular tachycardia episode may be about 0.25 seconds to about 0.5 seconds, such as about 0.4 seconds, although other time ranges are contemplated. The pressure sensing time window may restart if processor 80 detects another heart cycle (e.g., at the beginning of another R-wave) before the pressure sensing time window associated with the previous heart cycle expires.

Processor 80 may also characterize point P15 of EGM 140 as an R-wave of a heart cycle associated with the detected ventricular tachyarrhythmia event J. The detected heart cycle including the detected R-wave at point P15 may have a duration that qualifies the heart cycle as a ventricular tachycardia event. Point P16 may be the surrogate systolic pressure during the pressure cycle that corresponds to the heart cycle including the R-wave at point P15. That is, in FIG. 7A, the surrogate systolic pressure for pressure cycle W associated with the detected tachyarrhythmia event J is at point P16. Again, processor 80 may determine the surrogate systolic pressure by determining a highest pressure value during a pressure sensing time window that begins at the characterized R-wave at point P15.

The regularity of the pressure within right ventricle 28 during the detected ventricular tachycardia events may be determined based on the surrogate systolic pressure values at points P14 and P16. For example, if processor 80 determines that the surrogate systolic pressure values at points P14 and P16 are within a range of about 10%, then processor 80 may determine that the heart pressure within right ventricle 28 that is associated with the detected ventricular tachycardia events is relatively regular. In other examples, processor 80 may determine whether the pressure within right ventricle 28 is regular during the detected ventricular tachycardia episode based on surrogate diastolic pressures, surrogate pulse pressures or other values, such as an average pressure value within the pressure sensing time window.

In other examples, processor 80 may determine that the pressure associated with the ventricular tachycardia events is irregular if the difference between pressure values associated with each detected ventricular tachycardia event G-O and the mean pressure value or median pressure value associated with two or more of the detected ventricular tachycardia events G-O exceeds a threshold. Alternatively, processor 80 may determine whether the mean absolute difference between the pressure values associated with a respective one of two or more ventricular tachycardia events G-O exceeds a threshold percentage relative to the mean pressure value. Although two pressure values P14 and P16 are described with respect to FIG. 7A, in other examples, processor 80 may determine the pressure variability based on the pressure values associated with more than two tachyarrhythmia events.

As FIG. 7B further illustrates, the true heart cycles 142A/143A, 142B/143B, and 142D/143D may have substantially similar derivative values (dp/dt), which is generally the change of the pressure values over time. In contrast, the detected heart cycles based on electrical noise may have varying derivative values (dp/dt). For example, in the value shown in FIG. 7B, true heart cycle 142A/143A has a maximum change in pressure (dp/dt) of about 3, whereas electrical noise cycle from which tachyarrhythmia event J is detected has a maximum change in pressure of about 0.3. As another example, true heart cycle 142B/143B has a minimum change in pressure (dp/dt) of about −3, whereas electrical noise cycle from which tachyarrhythmia event G is detected has a minimum change in pressure of about 0. The values shown in FIG. 7B are merely shown for conceptual purposes to illustrate differences in pressure changes that may be present between true heart cycles and heart cycles detected based on actual noise. The numerical values shown in FIG. 7B are not intended to illustrate actual pressure change (dp/dt) values.

Processor 80 may determine that detected tachyarrhythmia events are true events if the change in pressure of the associated pressure cycles are within a particular range of a mean or median change in pressure of at least two or more detected tachyarrhythmia events. The range may be stored within memory 82 as a percentage of the mean or median change in pressure of at least two or more detected tachyarrhythmia events.

As conceptually shown in FIG. 7A, the pressure cycles are not associated with the noise cycles of EGM 140. Because electrical noise is not related to activity of heart 12, processor 80 may associate each detected tachyarrhythmia event that is detected based on noise with pressures at varying points along the pressure cycle of heart 12. In contrast, as shown in FIGS. 6A and 7A, a heart cycle in a regular sinus rhythm or during a tachyarrhythmia event may be associated with true pressure cycles of heart 12. Thus, the pressure value associated with each regular sinus rhythm or tachyarrhythmia event may be measured substantially similar points along a pressure cycle. As a result, the variance between pressures associated with each heart rhythm may be less than a predetermined threshold value. On the other hand, because electrical noise that is mischaracterized as a heart rhythm does not correspond to pressure cycles, heart pressures associated with the noise-based cycles may have a greater variation. For example, the surrogate diastolic and systolic pressures in the pressure sensing time windows associated with each detected noise rhythm may vary by more than the predetermined threshold value.

In some examples, processor 80 of IMD 16 may monitor a variance in the pressure within right ventricle 28 or another portion of heart 12 or the broader cardiovascular system to confirm that a detected arrhythmia episode is an actual arrhythmia episode. In addition, processor 80 of IMD 16 may monitor a pressure variance within heart 12 or cardiovascular system to determine whether therapy system 10 may be oversensing heart rhythms, e.g., due to compromised integrity of one of the leads 18, 20, 22 or due to another source of electrical noise. As described below, upon determining that the integrity of one of the leads 18, 20, 22 may be compromised or excessive noise is detected by sensing module 86 (FIG. 1), processor 80 may generate a sensing integrity indication.

The sensing integrity indication may be used for later analysis of therapy system 10 by a clinician or to generate an alert to patient 14 that therapy system 10 may need to be checked by a clinician. In some examples, processor 80 may recommend a corrective action upon alerting a clinician. For example, processor 80 may recommend that one of the leads 18, 20, 22 be checked for a loose connection with connector block 34 of IMD 16. In addition, in some examples, processor 80 may change the sensing electrode configuration (e.g., from a bipolar configuration to unipolar configuration) upon generating the sensing integrity indication.

Figure 8:
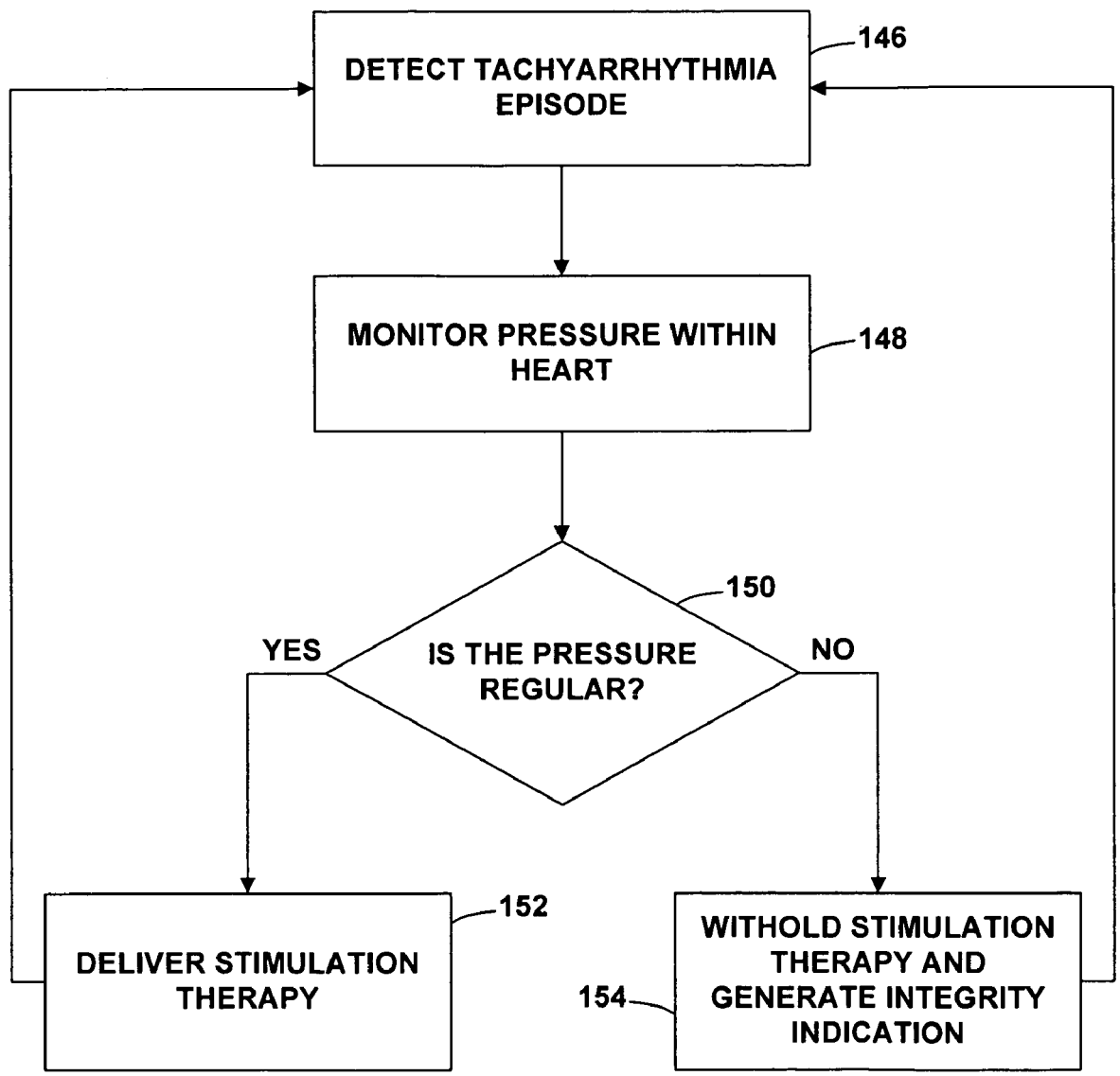
FIG. 8 is a flow diagram of an example technique for controlling therapy delivery to a heart of a patient based on a variance of pressure within the heart.

FIG. 8 is a flow diagram illustrating an example technique for controlling delivery of stimulation by IMD 16 based on a variance of cardiovascular pressure. While FIGS. 8-12 are described with reference to components of IMD 16, in other examples, another device may perform any part of the techniques described herein.

Processor 80 may detect a tachyarrhythmia episode (146), which may be, for example, a ventricular fibrillation episode, a ventricular tachycardia episode or a fast ventricular tachycardia episode. Processor 80 may implement any suitable technique to detect a tachyarrhythmia episode (146). In some examples, processor 80 may detect a tachyarrhythmia episode by determining a particular number of tachyarrhythmia events are detected. A tachyarrhythmia event may include a heart cycle that has an R-R interval that is less than a predetermined duration threshold value. Different threshold values may be used to characterize the heart cycle as a ventricular fibrillation event, a ventricular tachycardia event or a fast ventricular tachycardia event. The threshold duration values for determining whether an R-R interval qualifies the heart cycle as a tachyarrhythmia event may be stored within memory 82 of IMD 16. In other examples, other techniques for detecting a tachyarrhythmia episode may be used.

Upon detecting the tachyarrhythmia episode (146), processor 80 may determine the cardiovascular pressure values that are associated with the detected episode, e.g., by obtaining pressure data from pressure sensing module 92 (FIG. 4) (148). For example, processor 80 may review the pressure values collected during the tachyarrhythmia events of the episode. Pressure sensing module 92 may continuously provide processor 80 with pressure measurements within right ventricle 28 (or another region of heart 12) or pressure sensing module 92 may only provide the measurements to processor 80 upon interrogation of sensing module 92 by processor 80. In addition, pressure sensing module 92 may continuously measure pressure within right ventricle 28 or regular, periodic intervals.

Processor 80 may determine whether the cardiovascular pressures that are associated with the detected tachyarrhythmia events of the episode are relatively regular (150). In some examples, processor 80 may determine the regularity of pressures by determining whether the variance in pressure measurements associated with the tachyarrhythmia events is less than a threshold value, as described above. The pressure measurements that are monitored for variance may include, for example, at least one or more of systolic pressures, diastolic pressures, pulse pressures, average pressures over a pressure cycle, median pressure measurements within the pressure cycles, or combinations thereof.

Each tachyarrhythmia event, e.g., a heart cycle having a duration that is less than a threshold value, may be associated with a pressure cycle, from which a pressure value may be selected. If processor 80 determines that the sensed cardiovascular pressure values associated with the detected tachycardia events are relatively regular, processor 80 may control the delivery of stimulation therapy to patient (152). For example, if the tachyarrhythmia episode comprises ventricular tachycardia, processor 80 may control stimulation generator 84 to deliver pacing, cardioversion or defibrillation electrical signals to heart 12. As another example, if the tachyarrhythmia episode comprises ventricular fibrillation, processor 80 may control stimulation generator 84 to deliver defibrillation electrical signals to heart 12. Determining that the tachyarrhythmia events of the episode are correlated with relatively regular pressure values may help processor 80 confirm that the tachyarrhythmia episode is not a false positive, e.g., detected based on electrical noise.

If processor 80 determines that the sensed cardiovascular pressures associated with the detected tachycardia events are not relatively regular (150), processor 80 may withhold stimulation therapy and generate a sensing integrity indication (154). The irregular pressures associated with the tachyarrhythmia events may indicate, for example, that the detection of the arrhythmia was a false positive and attributable to noise. The sensing integrity indication may be stored within IMD 16, along with the associated date stamp and any other relevant information (e.g., pressure values), for later retrieval and analysis by a clinician. In addition, processor 80 may generate a notification to patient 14 that medical attention to identify the source of the inappropriately detected tachyarrhythmia episode may be desirable.

Figure 9:
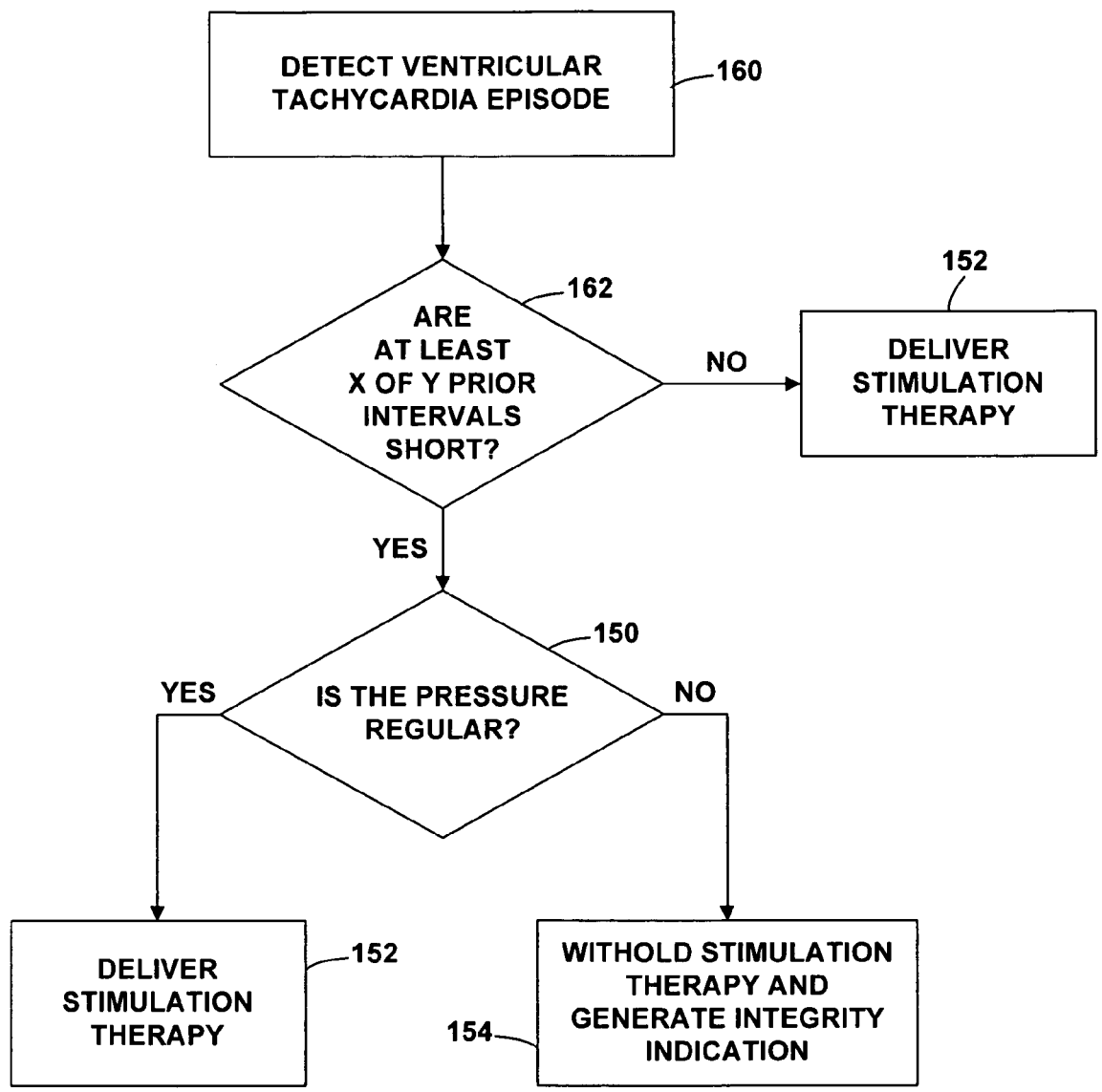
FIG. 9 is a flow diagram of another example technique for controlling therapy delivery to a heart of a patient upon the detection of a ventricular tachycardia episode based on a variance of pressure within the heart.

FIG. 9 is a flow diagram illustrating another example technique for controlling the delivery of stimulation therapy to heart 12 based on a sensed cardiovascular pressure. Processor 80 of IMD 16 may detect a ventricular tachycardia episode (160), which may be a type of tachyarrhythmia episode. Processor 80 may implement any suitable technique to detect a ventricular tachycardia episode (160). In some examples, processor 80 may detect a ventricular tachycardia episode by detecting a predetermined number of sequential ventricular tachycardia events. As previously indicated, a ventricular tachycardia event may include a cardiac cycle measured between successive R-waves that has a duration less than a predetermined ventricular tachycardia threshold value. In some examples, the ventricular tachycardia threshold value may be about 340 ms to about 400 ms, although other intervals are contemplated. In other examples, other techniques for detecting a ventricular tachycardia episode may be used.

Processor 80 may inappropriately characterize electrical noise attributable to a lead-related condition or other electromagnetic interference as a heart cycle that meets the limitations of a ventricular tachycardia event. If the detection of the ventricular tachycardia episode is attributable to electrical noise, there may be multiple sequential very short intervals or a relatively high percentage of short intervals (e.g., 6 of the last 8 rhythms may be short intervals). A short interval may be an interval less than a set value or less than a percentage of a programmed value (e.g., ventricular fibrillation detection interval) or a set value above a blanking period of IMD 16, as described below.

Detecting a tachyarrhythmia episode may be attributable to a lead related condition that may occur near a blanking period of sensing module 86 (FIG. 4). Processor 80 may account for the blanking period by characterizing R-R intervals that are determined to be less than a predetermined time period above the blanking period as a short interval. Accordingly, the threshold time period for determining whether an R-R interval was a short interval may include the blanking time period in addition to the determined time period above the blanking period. In some examples, processor 80 may determine an R-R interval is short if it is about 10 ms to about 50 ms above the blanking period, such as about 20 ms. Other predetermined time periods above the blanking period are contemplated. If the blanking period is set as 120 ms and the time period above the blanking period is about 20 ms, the predetermined threshold for classifying a detected tachyarrhythmia event as a short interval would be equal to approximately 140 ms.

Some heart rhythms that indicate a ventricular tachycardia episode may have fewer sequential short intervals or a fewer percentage of short intervals than the short intervals that are observed with electrical noise. Accordingly, if a threshold number (referred to as "X") of detected heart rhythms of a predetermined number (referred to as "Y") of the most recently detected heart rhythms are short intervals, the detected heart rhythms may be noise signals mischaracterized as tachyarrhythmia events.

In the technique shown in FIG. 9, upon detecting the ventricular tachycardia episode (160), processor 80 may determine whether at least X of the Y of the most recent R-R intervals constitute short intervals (162). "X" and "Y" are variables used to represent a predetermined number, which may be selected by a clinician and stored within memory 82 of IMD 16 or automatically selected by processor 80. The number "X" is less than the number "Y." For example, in some examples, processor 80 may determine whether at least 6 of the 8 of the most recent R-R intervals constitute short intervals (162). However, the "6 of 8" is merely one example, and other numbers for "X" and "Y" are contemplated.

In some examples, processor 80 may utilize a short interval counter to determine whether at least X of the prior Y number of R-R intervals are short intervals. For example, for each short interval detected, processor 80 may increment the counter. Upon analyzing the last Y intervals, processor 80 may determine the number of short intervals, as indicated by the counter.

Figure 10:
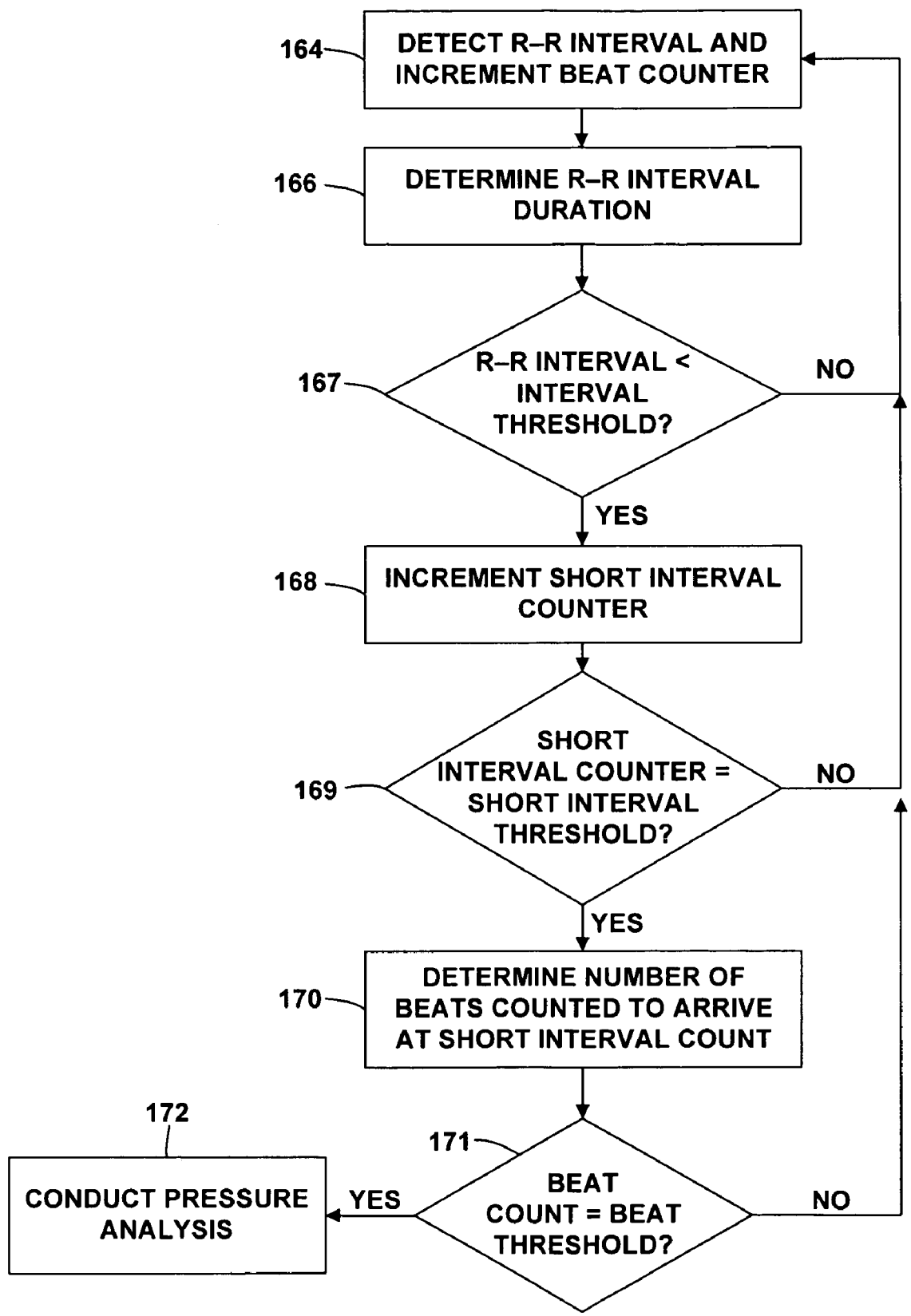
FIG. 10 is a flow diagram of an example technique for counting the number of short intervals.

In another example, as described with respect to FIG. 10, processor 80 may increment a counter for each short interval detected, and upon reaching X number of short intervals, processor 80 may determine how many R-R intervals were counted to reach X number of short intervals. If the number of intervals that were counted to reach X number of short intervals is less than the stored number Y, processor 80 may determine that at least X number of Y number of the prior R-R intervals were short intervals. On the other hand, if the number of intervals that were counted to reach X short intervals is greater than (or exceeds) the stored number Y, processor may determine that at least X number of the Y number of the prior R-R intervals were not short intervals.

In other examples, processor 80 may utilize a time window and determine the number of short intervals counted during the time window. The time window may be stored in memory 82 of IMD 16 and may be, for example, the average duration of Y intervals. An example of this counting technique is described at FIG. 5 of U.S. Pat. No. 7,369,893 to Gunderson, entitled, "METHOD AND APPARATUS FOR IDENTIFYING LEAD-RELATED CONDITIONS USING PREDICTION AND DETECTION CRITERIA," which issued on May 6, 2008 and is incorporated herein by reference in its entirety.

If processor 80 determines that at least X number out of the Y number of most recent R-R intervals were not short intervals, processor 80 may deliver stimulation therapy to heart 12 (152). If the at least X number out of the Y number of most recent R-R intervals were not short intervals, it may indicate that the ventricular tachycardia episode was detected based on actual heart signals, rather than electrical noise.

If processor 80 determines that at least X number out of the Y number of prior R-R intervals were short intervals, processor 80 may determine whether the cardiovascular pressures associated with the detected ventricular tachycardia events were regular (150). Processor 80 may use the techniques described above with respect to FIGS. 6-8 to determine if the pressure was regular, i.e., had a low variance. If processor 80 determines that the cardiovascular pressure associated with the detected tachycardia events were relatively regular, processor 80 may deliver stimulation therapy to patient (152). On the other hand, if processor 80 determines that the pressure is not regular (150), processor 80 may withhold stimulation therapy and generate an integrity indication (154). The irregular pressure may indicate, for example, that the detection of the ventricular tachycardia episode was a false positive and detected based on electrical noise.

In some examples of the technique shown in FIG. 9, in addition to or instead of determining whether at least X of the Y of the most recent R-R intervals constitute short intervals (162), processor 80 may determine whether the coupling interval between successive detected ventricular tachycardia events are variable. For example, processor 80 may determine whether the difference between the coupling intervals for two or more sets of successive ventricular tachycardia events exceeds a predetermined threshold value or percentage. A variable coupling interval between successive detected ventricular tachycardia events may indicate that the electrical signal sensed by sensing module 86 of IMD 16 (FIG. 4) is at least partially attributable to electrical noise and may not reflect electrical activity of heart 12. With some tachyarrhythmia episodes, the tachyarrhythmia events that make up the episode may have a relatively stable rhythm. This stable rhythm may be quantified as a coupling interval between successive tachyarrhythmia events that is within a particular threshold range (e.g., percentage or absolute value) of previous and successive coupling intervals. Accordingly, an unstable rhythm of the detected tachyarrhythmia events may indicate that sensing module 86 is sensing electrical noise.

As an example, IMD 16 may be programmed with a stability value, e.g., 50 ms, that indicates an acceptable coupling interval between successive detected ventricular tachycardia events. Upon counting a predetermined number of ventricular tachycardia events, processor 80 may evaluate the next coupling interval. If the difference between any of the previous three ventricular tachycardia events is greater than the stability value, processor 80 may reset the ventricular tachycardia counter to 0 because processor 80 may consider the detected ventricular tachycardia events unstable.

In other examples of FIG. 9, instead of determining whether a threshold number of short intervals were detected (162), processor 80 may implement another lead integrity determination technique, such as determining an impedance of one or more of the leads 18, 20, 22. If the measured lead impedance indicates that a potential sensing issue exists, processor 80 may initiate the evaluation of the pressure variance (150) as described with respect to FIG. 9.

FIG. 10 is a flow diagram illustrating a technique for determining whether at least X number of the Y number of prior R-R intervals were determined to be short intervals. For each detected heart cycle, processor 80 may increment a beat counter (164). The detected heart cycle may be, for example, each electrical signal that is measured between successive R-R intervals or other types of waves. The heart cycle may correspond to a heartbeat. After detecting an R-R interval, processor 80 may measure the duration of the R-R interval (166) and determine whether the R-R interval is less than a threshold time period (167). The predetermined threshold may be the duration of a short interval. In some examples, the predetermined time period may be approximately 120 ms to about 170 ms, such as about 140 ms. In other examples, a short interval may be characterized by the interval between other waves of the sinus rhythm (e.g., a P-P interval).

If the R-R interval is not less than the predetermined threshold and, therefore, is not near the blanking period of sensing module 86, e.g., within 20 ms of the blanking period, processor 80 may increment the beat counter (164) and measure a next R-R interval duration (166). Processor 80 may determine whether the next R-R interval is less than the predetermined interval threshold (164). Each time that an R-R interval is determined to be less than the predetermined interval threshold and therefore near the blanking period, a short interval counter is incremented (168).

After each increment of the short interval counter, processor 80 may determine whether the short interval counter is equal to a predetermined short interval threshold (169). As previously described, if at least X number of the Y number of prior R-R intervals are short, processor 80 may analyze the pressure associated with the detected tachyarrhythmia events to determine whether the detected tachyarrhythmia episode is a true episode or attributable to electrical noise. Thus, the short interval threshold may indicate the number of short intervals that are detected to proceed to a pressure analysis process. If the short interval counter is equal to the short interval threshold (169), processor 80 may determine how many R-R intervals were counted in order to arrive at the NID threshold (170), such as by referencing the beat counter. Processor 80 may compare the number of counted R-R intervals to a beat threshold (171) to determine whether at least X number of the Y number of prior R-R intervals were determined to be short intervals. For example, the short interval counter may be the "X" number and the beat threshold may be the "Y" number of most recent R-R intervals, which are related to heartbeats.

If the number of R-R intervals that were counted is equal to the beat threshold (171), processor 80 may determine that at least X number of the Y number of prior R-R intervals were determined to be a short interval, and determine that pressure analysis is desirable to determine whether the detected tachyarrhythmia events were appropriately used to detect the tachyarrhythmia episode (172). The pressure analysis may be, for example, a determination of whether the pressure associated with the tachyarrhythmia events had a variability below a predetermined threshold, as described above with respect to FIG. 9. If the number of R-R intervals that were counted is not equal to the beat threshold (171), processor 80 may monitor the next R-R interval (164), and determine whether the R-R interval is less than a short interval threshold (167).

Figure 11:
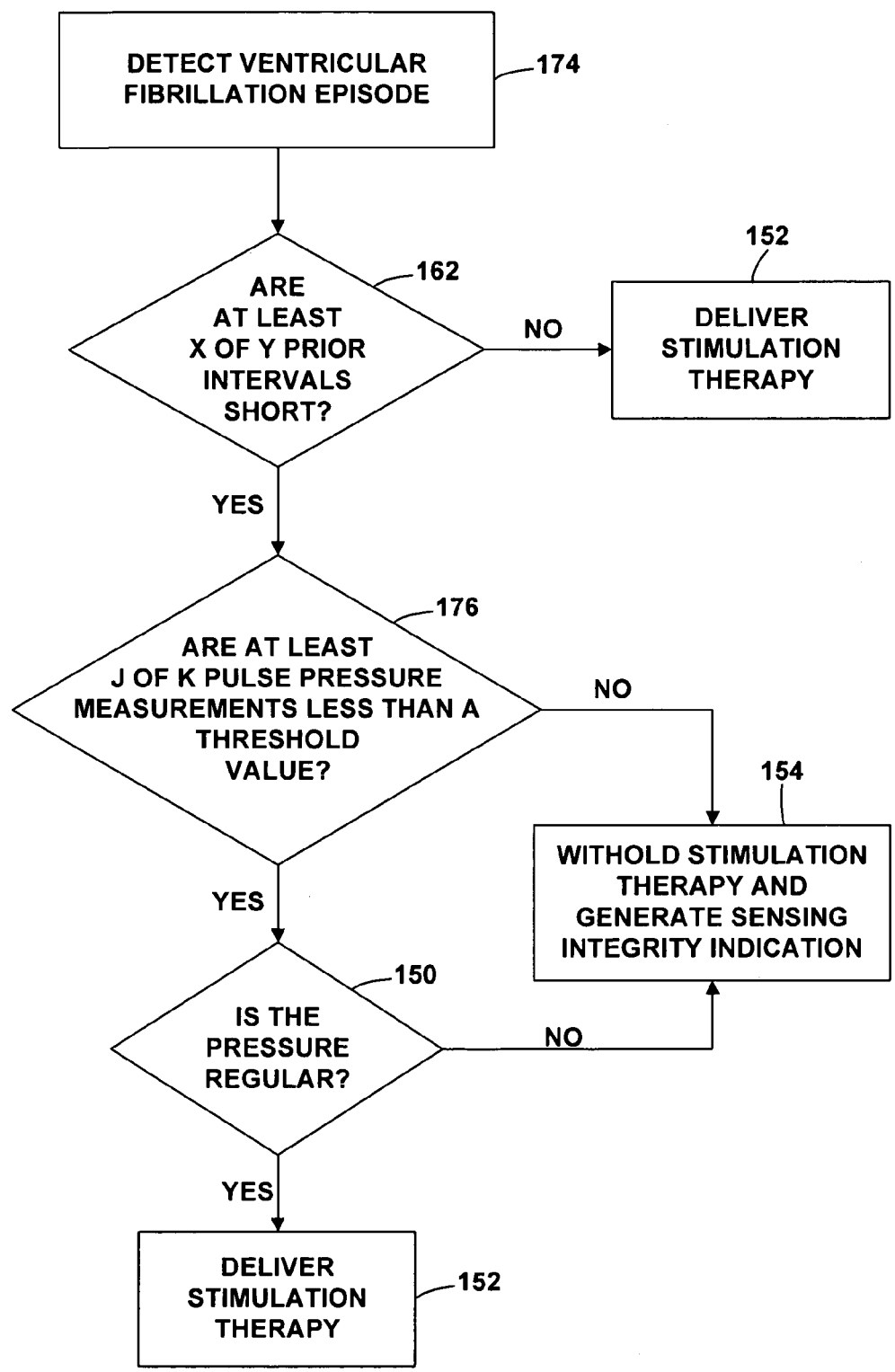
FIG. 11 is a flow diagram of another example technique for controlling therapy delivery to a heart of a patient upon the detection of a ventricular fibrillation episode based on a variance of pressure within the heart.

FIG. 11 is a flow diagram illustrating another example technique for controlling the delivery of stimulation therapy to heart 12 based on a variability of a sensed cardiovascular pressure. Processor 80 of IMD 16 may detect a ventricular fibrillation episode (174), which may be a type of tachyarrhythmia episode. Processor 80 may implement any suitable technique to detect a ventricular fibrillation episode (174). In some examples, processor 80 may detect the ventricular fibrillation episode by detecting a particular number of ventricular tachycardia events within a particular time frame, which may be measured as by a number of heart cycles.

As an example, processor 80 may detect a ventricular fibrillation episode upon detecting about "A" number of ventricular fibrillation events within the "B" number of most recent cardiac depolarization events. For example, "A" may be about 10 and "B" may be about 15. However, in other examples, processor 80 may use different values of "A" and "B" to detect a ventricular fibrillation episode. A ventricular fibrillation event may include a cardiac cycle measured between successive R-waves (sometimes referred to fib waves in the case of fibrillation) that has a duration less than a predetermined ventricular fibrillation threshold value. The ventricular fibrillation episode may be less than the ventricular tachycardia threshold used to characterize a cardiac cycle as a ventricular tachycardia event. In some examples, the ventricular fibrillation threshold value may be about 280 ms to about 320 ms, although other intervals are contemplated. In other examples, other techniques for detecting a ventricular fibrillation episode may be used.

Upon detecting the ventricular fibrillation episode (174), processor 80 may determine whether at least X number of the Y number of prior R-R intervals constitute short intervals (162). As described above, processor 80 may interpret electrical noise as a heart rhythm having multiple sequential short intervals or a relatively high percentage of short intervals (e.g., 6 of the last 8 rhythms may be short intervals). Processor 80 may utilize any of the techniques described with respect to FIGS. 9 and 10 to count the number of short intervals.

In some examples, if the number of short intervals does not meet the threshold limitation, e.g., at least X number of the Y number of most recent electrical signal intervals (e.g., detected "R-R" intervals, which may or may not be true R-R intervals of a heart rhythm) are not short intervals, processor 80 may determine whether a certain percentage of pulse pressure measurements was less than a threshold pulse pressure value (176). For example, in the technique shown in FIG. 11, processor 80 may determine whether at least "J" number of the "K" number of the last pulse pressure measurements were less than a threshold pulse pressure value. "J" and "K" are variables used to represent a predetermined number, which may be selected by a clinician or automatically selected by processor 80. The number "J" is less than the number "K." The K number of last pulse pressure measurements may be, for example, the pulse pressure measurements associated with each if the K number of prior detected ventricular fibrillation events, which may or may not be detected based on an actual heart rhythm (e.g., may be detected based on electrical noise). In another example, the K number of last pulse pressure measurements may be, the pulse pressure measurements associated with each if the K number of prior detected R-R intervals, which may or may not be detected based on an actual heart rhythm.

In some examples, processor 80 may determine whether at least five of the last eight pulse pressure measurements, were less than about 6 millimeters of mercury (mmHg). Five of eight and 6 mmHg as the thresholds are merely examples. Processor 80 may utilize any suitable counting technique, such as techniques similar to those described with respect to FIGS. 9 and 10 for counting short intervals. In other examples, other threshold pulse pressure values may be used. The threshold pulse pressure values may be specific to a patient or may be general to two or more patients. The threshold pulse pressure values may be determined, e.g., based on determining the pulse pressure values of the one or more patients during the confirmed ventricular fibrillation episode for each of the one or more patients.

Ventricular fibrillation may be associated with relatively low pulse pressure values, as well as low systolic pressure values, and, in some cases, low diastolic pressure values. During ventricular fibrillation, the cardiac muscle in right ventricle 28 and left ventricle 32 (FIG. 2) may exhibited uncoordinated contraction. The uncoordinated contraction of the heart muscle may cause heart 12 to exhibit relatively low pressure due to the poor contraction of the heart, and, therefore, the low flow of blood through heart 12. Accordingly, if the patient is in a true ventricular fibrillation episode, the pulse pressure values associated with the ventricular fibrillation events of the episode are likely to be less than a threshold pulse pressure value, such as about 6 mmHg. Other threshold pulse pressure values may be used in other examples, and, in some cases, may be specific to a particular patient 14.

In other examples, processor 80 may determine whether a certain percentage of other types of pressure measurements (or their derivatives) were less than a threshold pressure value, such as systolic or diastolic pressures, or a combination of the systolic, diastolic, and/or pulse pressures. In addition, in other examples, rather than determining whether the pressure values (e.g., pulse pressure, systolic, diastolic or a combination thereof) were less than a pressure threshold value, thereby indicating a ventricular fibrillation episode, processor 80 may determine whether the pressure values were greater than a pressure threshold value, thereby indicating the absence of a ventricular fibrillation episode.

If the number of pulse pressure measurements that were less than the threshold pulse pressure value does not meet the threshold limitation, e.g., at least J number of the K number of prior pulse pressure measurements were not less than a threshold pulse pressure value, processor 80 may control stimulation generator 84 to withhold stimulation (154). For example, if fewer than the threshold number of pulse pressure measurements were less than the threshold pulse pressure value, processor 80 may determine that the detected ventricular fibrillation events were associated with pressure values that were too high to be true ventricular fibrillation events. Thus, processor 80 may determine that the electrical signals used to detect the ventricular fibrillation episode were at least partially attributable to electrical noise. In this way, the pulse pressure values may indicate whether the ventricular fibrillation episode was attributable to electrical noise. Processor 80 may also generate an integrity indication (154), which may be stored in memory 82 or transmitted to programmer 24 or another device to notify patient 14 or a clinician of a potential sensing issue.

If the number of pulse pressure measurements that were less than the threshold pulse pressure value exceeds the threshold number, e.g., at least J number of the K number of prior pulse pressure measurements were less than a threshold value, processor 80 may determine that the electrical signals rhythms used to detect the ventricular fibrillation episode may be attributable to actual heart rhythms. Accordingly, upon determining that the number of pulse pressure measurements that were less than the threshold pulse pressure value meets the threshold limitation, processor 80 may determine whether the pressure associated with the detected ventricular fibrillation events was regular (150).

In other examples of the technique shown in FIG. 11, processor 80 may not determined whether a certain percentage of pulse pressure measurements was less than a threshold pulse pressure value (176).

Processor 80 may use the techniques described above with respect to FIGS. 7 and 9 to determine if the pressure was regular. If processor 80 determines that the cardiovascular pressure values associated with the detected ventricular fibrillation events was regular, e.g., had a low variability, processor 80 may deliver stimulation therapy to patient (152). On the other hand, if processor 80 determines that the pressure values associated with the detected ventricular fibrillation events were not regular, e.g., had a variability above a threshold variability value (150), processor 80 may withhold stimulation therapy and generate an integrity indication (154). The irregular heart pressure may indicate, for example, that the detection of the ventricular fibrillation events, and, therefore, the ventricular fibrillation episode, were false positives and detected based on electrical noise.

Figure 12:
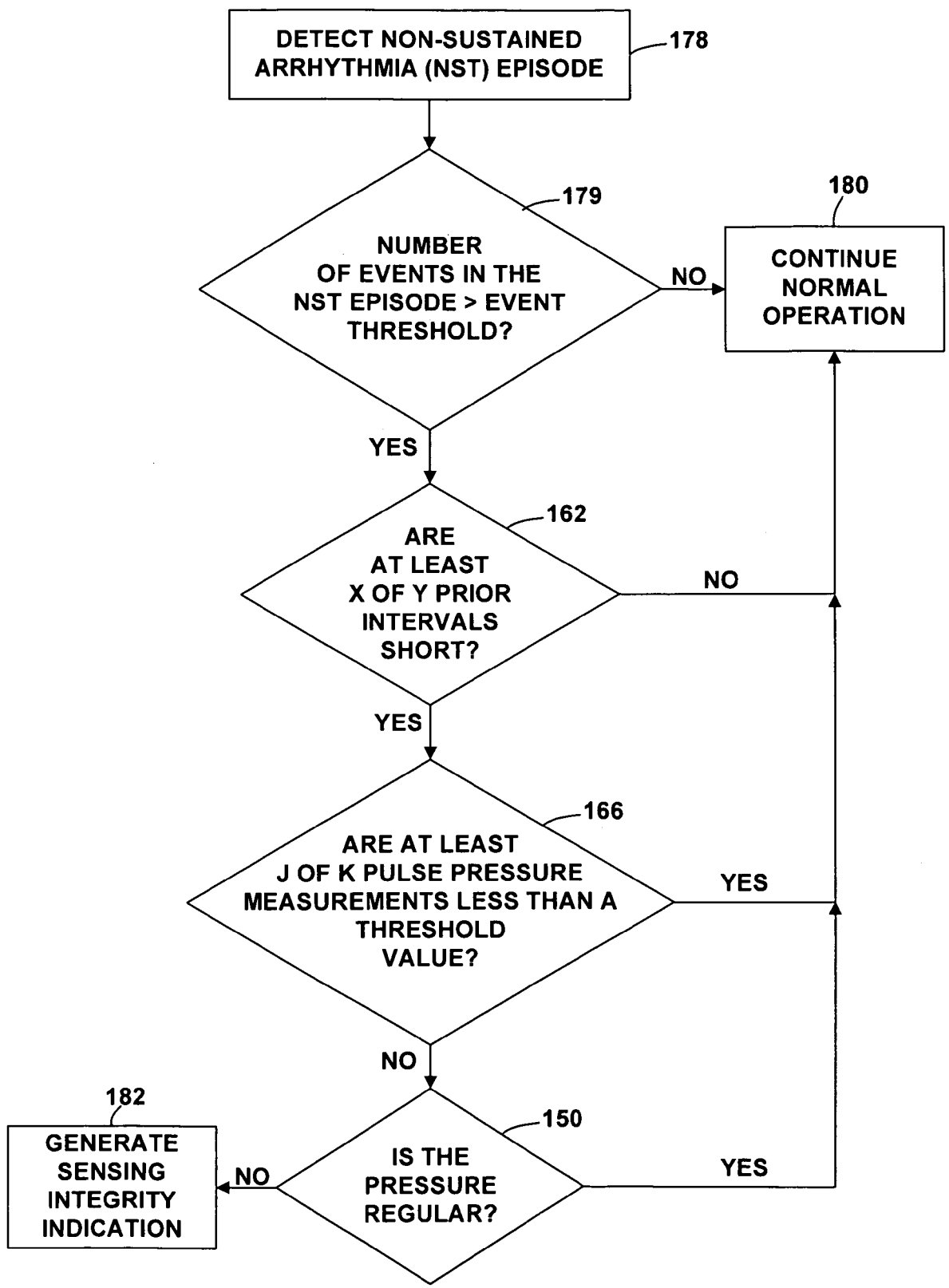
FIG. 12 is a flow diagram of an example technique for generating a sensing integrity indication based on the detection of a non-sustained tachyarrhythmia episode and a variance of pressure within the heart.

FIG. 12 is a flow diagram of an example technique for generating a sensing integrity indication based on the detection of a non-sustained tachyarrhythmia (NST) episode and a cardiovascular pressure. The technique shown in FIG. 12 may be useful for detecting a lead integrity issue or electrical noise issue prior to the occurrence of a tachyarrhythmia episode that would qualify for delivery of a responsive therapy. A NST episode may be, for example, a train of tachyarrhythmia events that do not meet the requirements for being characterized as a tachyarrhythmia episode that would qualify for delivery of a responsive therapy. In some examples, during a normal detection process, processor 80 may detect a tachyarrhythmia episode by comparing time intervals between successive R-waves (or other types of heart waves) to a set of programmable detection intervals, which may be stored in memory 82 of IMD 16 (FIG. 4). For example, when an R-R interval between R waves of successive cardiac rhythms is between about 320 ms and about 400 ms, processor 80 may determine that a ventricular tachycardia event was detected and increment a ventricular tachycardia interval counter. Once a certain number ventricular tachycardia events, e.g., sensed events having a ventricular tachycardia time interval, are detected (e.g., about 16 events), processor 80 may determine that a ventricular tachycardia episode is detected.

Processor 80 may identify a NST and store a NST episode indication within a NST episode log when less than a required number of tachyarrhythmia events are detected (e.g., less than 16 events), but more than a predetermined number of tachyarrhythmia events are detected (e.g., about 5). The NST episode log may be stored within memory 82 of IMD 16 (FIG. 4) and store information relating to the NST episodes, including a date/time stamp and an average cycle length of each non-sustained episode.

In the example technique shown in FIG. 12, processor 80 may detect a NST episode (178) using any suitable technique. In some examples, processor 80 may determine whether an ECG signal indicated heart activity that was fast enough to fall within a ventricular tachycardia or ventricular fibrillation zones of time intervals without meeting the threshold number of intervals for the ventricular tachycardia or ventricular fibrillation episode. In some examples, processor 80 may identify a NST episode if at least five cardiac cycles within a particular time frame or within a particular number of cardiac cycles met the limitations of qualifying as a ventricular tachycardia or ventricular fibrillation event.

Upon detecting the NST episode (178), processor 80 may determine whether there are a threshold number of tachyarrhythmia events in the NST episode to merit an analysis of the associated cardiovascular pressures (179). For example, processor 80 may determine the number of R-R intervals that fell within the ventricular tachycardia or ventricular fibrillation event zones and compare that number to an event threshold value, which may be stored within memory 82 of IMD 16. If the number of tachyarrhythmia events in the NST episode does not exceed (i.e., is less than) the event threshold, processor 80 may continue normal operation of controlling stimulation generator 84 (180). In other examples, processor 80 may eliminate the determination of whether there are a threshold number of tachyarrhythmia events in the NST episode to merit an analysis of the associated cardiovascular pressures and determine the cardiovascular pressures associated with the tachyarrhythmia events of the NST episode upon detecting the NST episode.

Upon detecting the NST episode (178), processor 80 may determine whether a threshold percentage of the prior detected R-R intervals constitute short intervals. The detected R-R intervals may not be true R-R intervals of a heart signal, but may be detected R-R intervals of an electrical signal that sensing module 86 of IMD 16 (FIG. 4) characterizes as heart signals. In some examples, processor 80 may determine whether at least X number of the Y number of prior R-R intervals constitute short intervals (162), as described above with respect to FIGS. 9 and 10.

If at least X number of the Y number of prior R-R intervals are not short intervals (162), processor 80 may continue normal operation of controlling stimulation generator 84 (180). If at least X number of the Y number of prior R-R intervals are short intervals (162), processor 80 may determine whether the pulse pressure measurements associated with a predetermined number of detected cardiac cycles are less than a threshold pulse pressure value, e.g., using the techniques described with respect to FIG. 11. In the example technique shown in FIG. 12, if at least J number of the K number of prior pulse pressure measurements were less than a threshold pulse pressure value, processor 80 may determine that sensing module 86 did not characterize electrical noise as heart signals and that the detected NST episode is a true NST. Again, this may be because some true tachyarrhythmia events, such as ventricular fibrillation events, may be associated with a relatively low pulse pressure. Thus, if at least J number of the K number of prior pulse pressure measurements were less than a threshold pulse pressure value, processor 80 may determine that the pulse pressure values indicate the detected tachyarrhythmia events were true events. Processor 80 may then continue normal operation of controlling stimulation generator 84 (180).

If processor 80 determines that at least J number of the K number of prior pulse pressure measurements were not less than a threshold pulse pressure value, processor 80 may determine that the detected NST episode may not be a true NST. Accordingly, processor 80 may implement other checks to determine whether the detected NST episode was attributable to electrical noise. For example, in the example shown in FIG. 12, processor 80 may determine whether the pressure associated with the heart rhythms of the NST episode was regular (150), e.g., using the techniques described above with respect to FIG. 8. If the pressure was regular, processor 80 may determine that sensing module 86 did not characterize electrical noise as heart signals, and processor 80 may continue normal operation of controlling stimulation generator 84 (180). If the pressure was not regular, processor 80 may generate a sensing integrity indication (182).

The sensing integrity indication may be used to generate a patient notification. In some examples, for each sensing integrity indication that is generated, processor 80 increments a counter. Upon reaching a predetermined threshold number of sensing integrity indications, processor 80 may control telemetry module 88 (FIG. 4) to transmit a signal to programmer 24 or another device. The predetermined threshold number of sensing integrity indications that trigger the generation of a patient or clinician notification may be selected by a clinician or otherwise programmed into IMD 16. In some examples, an alert may be generated upon the generation of a single sensing integrity indication by processor 80 of IMD 16. In other examples, an alert may be generated upon the generation of multiple sensing integrity indications (e.g., two or more) by processor 80 of IMD 16.

Upon receiving a signal from IMD 16 that indicates the threshold number of sensing integrity indications were generated, programmer 24 may provide a notification to patient 14 that indicates that the sensing integrity of IMD 16 may be potentially compromised and needs to be checked by a clinician. In addition or alternatively, processor 80 may transmit a signal to programmer 24 or another computing device, which may then directly transmit the notification to the clinician. A notification may be generated by programmer 24 and may be, e.g., in the form of an audible sound, visual alert (e.g., a flashing light), a somatosensory alert (e.g., a mechanical vibration) or a combination of the audible, visual, and/or somatosensory alerts. Alternatively, other alert techniques may be employed.

In some examples, processor 80 may recommend a corrective action upon alerting a clinician. For example, with the notification that a potential sensing issue has been detected, processor 80 may generate a recommendation that one of the leads 18, 20, 22 should be checked for a loose connection with connector block 34 of IMD 16 or the electrical insulation of one of the leads 18, 20 or 22 should be checked.

In some examples, the generating of the sensing integrity indication (182) may be used to control therapy delivery to heart 12. As an example, processor 80 may change the sensing or therapy electrode configuration (e.g., from a bipolar configuration to unipolar configuration) upon generating the sensing integrity indication. As another example, processor 80 may implement other lead integrity checks to further evaluate the sensing integrity of system 10. For example, processor 80 may initiate a check of the impedance of one or more of the leads 18, 20, 22.

In other examples of the technique shown in FIG. 12, a sensing integrity indication may be generated without determining whether a threshold percentage of the most recent R-R intervals constitute short intervals (162) and/or whether the pulse pressure measurement associated with a predetermined number of previous heart rhythms are less than a threshold pulse pressure threshold (176). For example, after determining that the detected NST episode includes a threshold number of tachyarrhythmia events, processor 80 may determine whether the heart pressure associated with the events or other detected heart cycles were regular (150). In some examples, processor 80 determines a variance of the heart pressure values associated with the detected R-R intervals to determine whether the pressure is regular (150).

While the techniques shown in FIGS. 8-12 are described as being performed by processor 80 of IMD 16, in other examples, a processor of another device, such as processor 100 of programmer 24 (FIG. 5) or a clinician workstation may perform any part of the techniques shown in FIGS. 8-12 or otherwise described herein. For example, processor 100 of programmer 24 may receive an EGM from sensing module 86 of IMD 14 and a pressure signal from pressure sensor 30 to determine whether the pressure associated with a detected tachyarrhythmia episode or a NST episode was variable (150) (FIG. 8). Further, processor 100 of programmer 24 or another device may generate a sensing integrity indication upon determining that a detected tachyarrhythmia episode or a NST episode may have been detected based on electrical noise.

Figure 13:
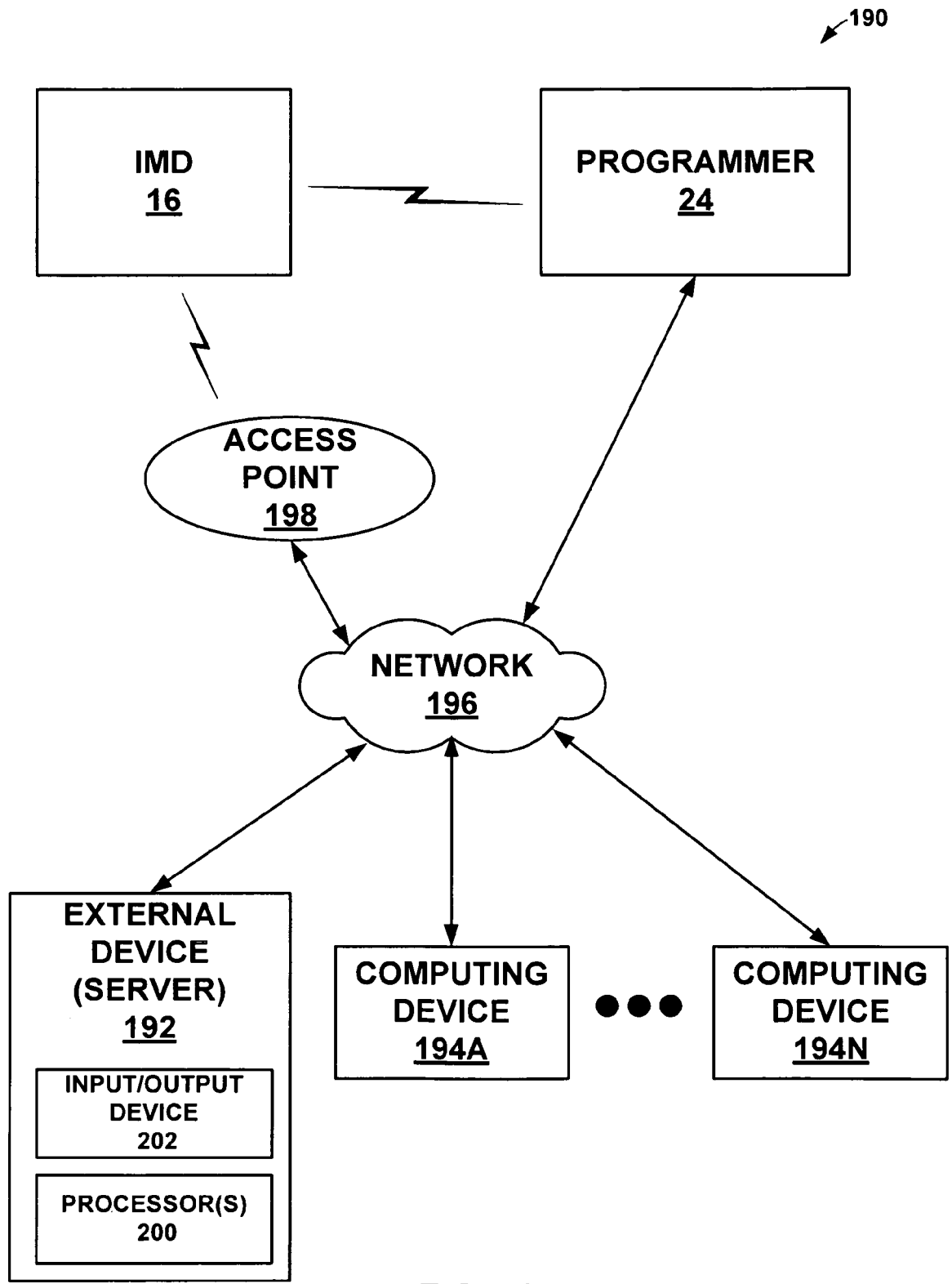
FIG. 13 is a block diagram illustrating an example system that includes an external device, such as a server, and one or more computing devices that are coupled to the IMD and programmer shown in FIG. 1 via a network.

FIG. 13 is a block diagram illustrating a system 190 that includes an external device 132, such as a server, and one or more computing devices 194A-194N that are coupled to IMD 16 and programmer 24 shown in FIG. 1 via a network 196, according to one embodiment. In this embodiment, IMD 16 uses its telemetry module 88 to communicate with programmer 24 via a first wireless connection, and to communicate with an access point 198 via a second wireless connection. In the example of FIG. 13, access point 198, programmer 24, external device 192, and computing devices 194A-194N are interconnected, and able to communicate with each other, through network 196. In some cases, one or more of access point 198, programmer 24, external device 192, and computing devices 194A-194N may be coupled to network 196 through one or more wireless connections. IMD 16, programmer 24, external device 192, and computing devices 194A-194N may each comprise one or more processors, such as one or more microprocessors, DSPs, ASICs, FPGAs, programmable logic circuitry, or the like, that may perform various functions and operations, such as those described herein.

Access point 198 may comprise a device that connects to network 196 via any of a variety of connections, such as telephone dial-up, digital subscriber line (DSL), or cable modem connections. In other examples, access point 198 may be coupled to network 130 through different forms of connections, including wired or wireless connections. In some examples, access point 198 may communicate with programmer 24 and/or IMD 16. Access point 198 may be co-located with patient 14 (e.g., within the same room or within the same site as patient 14) or may be remotely located from patient 14. For example, access point 198 may be a home monitor that is located in the patient's home or is portable for carrying with patient 14.

During operation, IMD 16 may collect, measure, and store various forms of diagnostic data. For example, as described previously, IMD 16 may collect cardiovascular pressure values from pressure sensing module 92 (FIG. 4). In certain cases, IMD 16 may directly analyze collected diagnostic data and generate any corresponding reports or alerts. In some cases, however, IMD 16 may send diagnostic data to programmer 24, access point 198, and/or external device 192, either wirelessly or via access point 198 and network 196, for remote processing and analysis.

For example, IMD 16 may send programmer 24 collected cardiovascular pressure data and associated EGM data, which is then analyzed by programmer 24. Programmer 24 may generate reports or alerts after analyzing the pressure data and determining that there may be a possible condition with one or more of leads 18, 20, and 22, e.g., based on the variability of the pressure values that are associated with detected tachyarrhythmia events. As another example, IMD 16 may send the sensing integrity indication generated by processor 80 (FIG. 4) to programmer 24, which may take further steps to determine whether there may be a possible condition with one or more of leads 18, 20, and 22. For example, programmer 24 may initiate lead impedance tests or IMD 16 may provide lead impedance information, if such information is already available.

In some cases, IMD 16 and/or programmer 24 may combine all of the diagnostic data into a single displayable lead integrity report, which may be displayed on programmer 24. The lead integrity report contains diagnostic information concerning one or more electrode leads that are coupled to IMD 16, such as leads 18, 20, or 22. A clinician or other trained professional may review and/or annotate the lead integrity report, and possibly identify any lead-related conditions.

In another example, IMD 16 may provide external device 192 with collected diagnostic data via access point 198 and network 196. External device 192 includes one or more processors 200. In some cases, external device 192 may request such data, and in some cases, IMD 16 may automatically or periodically provide such data to external device 192. Upon receipt of the diagnostic data via input/output device 202, external device 192 is capable of analyzing the data and generating reports or alerts upon determination that there may be a possible condition with one or more of leads 18, 20, and 22. For example, one or more of leads 18, 20, and 22 may experience a condition related to a lead fracture or an insulation breach.

In one embodiment, external device 192 may combine the diagnostic data into a lead integrity report. One or more of computing devices 194A-194N may access the report through network 196 and display the report to users of computing devices 194A-194N. In some cases, external device 192 may automatically send the report via input/output device 202 to one or more of computing devices 194A-194N as an alert, such as an audio or visual alert. In some cases, external device 192 may send the report to another device, such as programmer 24, either automatically or upon request. In some cases, external device 192 may display the report to a user via input/output device 196.

In one embodiment, external device 192 may comprise a secure storage site for diagnostic information that has been collected from IMD 16 and/or programmer 24. In this embodiment, network 196 may comprise an Internet network, and trained professionals, such as clinicians, may use computing devices 194A-194N to securely access stored diagnostic data on external device 192. For example, the trained professionals may need to enter usernames and passwords to access the stored information on external device 192. In one embodiment, external device 192 may be a CareLink server provided by Medtronic, Inc., of Minneapolis, Minn.

As described herein, electrical noise may be discriminated from sensed heart signals based on cardiovascular pressure. In some examples described herein, a variance in the cardiovascular pressure values associated with a plurality of detected tachyarrhythmia events, e.g., above a threshold range, may indicate that the detected tachyarrhythmia events are at least partially attributable to electrical noise. In other examples, other characteristics of cardiovascular pressure may be used to discriminate electrical noise from sensed heart signals.

For example, in some examples, a mean or median value of the cardiovascular pressure values associated with a plurality of detected tachyarrhythmia events of a tachyarrhythmia episode may be compared to a threshold value to determine whether the tachyarrhythmia events were detected based on electrical noise. If mean or median value of the cardiovascular pressure values falls below the threshold value, which may be the threshold pressure value associated with a ventricular fibrillation or a ventricular tachycardia event, processor 80 of IMD 16 or another device may determine that the detected tachyarrhythmia events were true episodes. On the other hand, if the mean or median value of the cardiovascular pressure values is greater than the threshold value, processor 80 of IMD 16 may determine that the detected tachyarrhythmia events were not associated with a true tachyarrhythmia event, and, therefore, the tachyarrhythmia events were detected based on electrical noise.

As previously described, although many of the cardiovascular monitoring and analysis techniques described herein are performed by processor 80 of IMD 16, in other examples, another device may perform any part of the techniques described herein. For example, if pressure sensing module 92 (FIG. 4) is enclosed within a separate housing from IMD 16, pressure sensing module 92 may include a separate processor that analyzes the signals from pressure sensor 38. The processor of a separate pressure sensing module 92 may perform any one or more of the techniques described herein. In some examples, a sensing device may include pressure sensing module 92 and sensing module 86 (FIG. 4) in a common housing that does not include stimulation generator 84 (FIG. 4). The sensing device may include a processor that controls the generation and transmission of control signals to IMD 16 to control when stimulation generator 84 generates and delivers stimulation to heart 14 (FIG. 1). The processor of the sensing device may, for example, discriminate electrical noise from heart signals using any of the techniques described herein.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
    detecting a tachyarrhythmia episode of a heart of a patient, wherein the tachyarrhythmia episode comprises a plurality of detected tachyarrhythmia events;
    analyzing a plurality of cardiovascular pressure values, each of the cardiovascular pressure values being associated with a respective one of the detected tachyarrhythmia events, wherein analyzing the plurality of cardiovascular pressure values comprises determining a variability in the plurality of cardiovascular pressure values; and
    determining, based on the variability in the plurality of cardiovascular pressure values, whether the detected tachyarrhythmia episode is a false positive detection attributable to electrical noise.

2. The method of claim 1, further comprising controlling therapy delivery to the patient in response to the detected tachyarrhythmia episode based on determining whether the detected tachyarrhythmia episode is the false positive detection attributable to electrical noise.

3. The method of claim 2, wherein controlling therapy delivery comprises controlling a medical device to deliver therapy to the patient.

4. The method of claim 2, wherein controlling therapy delivery comprises controlling a medical device to withhold therapy delivery to the patient.

5. The method of claim 1, further comprising generating a patient or clinician alert.

6. The method of claim 1, wherein the tachyarrhythmia episode comprises at least one of a ventricular fibrillation episode, a ventricular tachycardia episode, a fast ventricular tachycardia episode or a non-sustained tachyarrhythmia episode.

7. The method of claim 1, wherein the each of the cardiovascular pressure values comprises at least one of a pulse pressure value, an average pressure value, a systolic pressure value, or a diastolic pressure value.

8. The method of claim 1, wherein the plurality of detected tachyarrhythmia events comprises a first detected tachyarrhythmia event and a second detected tachyarrhythmia event, and wherein determining the variability in the plurality of cardiovascular pressure values comprises determining whether a first cardiovascular pressure value of the plurality of cardiovascular pressure values associated with the first detected tachyarrhythmia event and a second cardiovascular pressure value of the plurality of cardiovascular pressure values associated with the second detected tachyarrhythmia event are within a threshold range of each other.

9. The method of claim 1, wherein determining the variability in the plurality of cardiovascular pressure values comprises determining whether the cardiovascular pressure associated with at least one detected tachyarrhythmia event of the plurality of detected tachyarrhythmia events varies by a threshold percentage compared to an average pressure value of cardiovascular pressures associated with at least two other detected tachyarrhythmia events of the plurality of detected tachyarrhythmia events.

10. The method of claim 9, wherein the threshold percentage comprises a percentage of between about five percent and about twenty-five percent.

11. The method of claim 1, wherein determining the variability in the plurality of cardiovascular pressure values comprises determining whether at least one of a mean or a median value of the plurality of cardiovascular pressure values is within a threshold range of values.

12. The method of claim 1, wherein determining the variability in the plurality of cardiovascular pressure values comprises:
    determining at least one of a mean value or a median value of at least two cardiovascular pressure values of the plurality of cardiovascular pressure values,
    determining a plurality of absolute difference values, wherein each absolute difference value of the plurality of absolute difference values comprises an absolute difference between a respective cardiovascular pressure value of the plurality of cardiovascular pressure values and the at least one of the mean value or the median value of the at least two cardiovascular pressure values, and
    comparing each absolute difference value of the plurality of absolute difference values to a threshold value or a threshold range of values.

13. The method of claim 1, wherein determining the variability in the plurality of cardiovascular pressure values comprises:
    determining at least one of a mean value or a median value of at least two cardiovascular pressure values of the plurality of cardiovascular pressure values,
    determining a plurality of absolute difference values, wherein each absolute difference value of the plurality of absolute difference values comprises an absolute difference between a respective cardiovascular pressure value of the plurality of pressure values and the at least one of the mean value or the median value of the at least two cardiovascular pressure values;
    determining at least one of a mean value or a median value of the plurality of absolute difference values, and
    determining whether the at least one of the determined mean value or the determined median value of the plurality of absolute difference values is within a threshold range of the at least one of the mean value or the median value of the at least two cardiovascular pressure values of the plurality of cardiovascular pressure values.

14. The method of claim 13, wherein the threshold range comprises a percentage of about five percent to about twenty-five percent of the at least one of the mean value or the median value of the at least two cardiovascular pressure values of the plurality of cardiovascular pressure values.

15. The method of claim 1, further comprising:
    determining whether any of the plurality of detected tachyarrhythmia events comprises a short interval;
    generating a count of a number of the detected tachyarrhythmia events that comprise a short interval; and
    analyzing the plurality of cardiovascular pressure values if the count is greater than or equal to a threshold value.

16. The method of claim 1, further comprising:
    comparing each cardiovascular pressure value of the plurality of cardiovascular pressure values to a first threshold pressure value;

generating a count of a number of cardiovascular pressure values of the plurality of cardiovascular pressure values that are less than or equal to the first threshold pressure value; and analyzing the plurality of cardiovascular pressure values if the count is greater than or equal to a second threshold value.

17. The method of claim 1, wherein determining, based on the variability in the plurality of cardiovascular pressure values, whether the detected tachyarrhythmia episode is the false positive detection attributable to electrical noise comprises:

determining whether the variability in the plurality of cardiovascular pressure values is greater than a threshold variability value;

determining that the detected tachyarrhythmia episode is the false positive detection attributable to electrical noise if the variability in the plurality of cardiovascular pressure values is greater than the threshold variability value; and determining that the detected tachyarrhythmia episode is not the false positive detection attributable to electrical noise if the variability in the plurality of cardiovascular pressure values is less than the threshold variability value.

18. The method of claim 1, wherein determining the variability in the plurality of cardiovascular pressure values comprises determining a peak-to-peak variability in the plurality of cardiovascular pressure values.

19. A system comprising:

a pressure sensor configured to generate a signal indicative of cardiovascular pressure within a heart of a patient; and a processor configured to detect a tachyarrhythmia episode of the heart of the patient, wherein the tachyarrhythmia episode comprises a plurality of tachyarrhythmia events, wherein the processor is further configured to analyze a plurality of cardiovascular pressure values based on the signal generated by the pressure sensor by at least determining a variability in the plurality of cardiovascular pressure values, each of the cardiovascular pressure values being associated with a respective one of the tachyarrhythmia events, and wherein the processor is further configured to determine, based on the variability of the plurality of cardiovascular pressure values, whether the detected tachyarrhythmia episode is a false positive detection attributable to electrical noise.

20. The system of claim 19, further comprising a medical device, wherein the processor is further configured to control the medical device to deliver therapy to the patient in response to detecting the tachyarrhythmia episode based on determining whether the detected tachyarrhythmia episode is a false positive detection attributable to electrical noise.

21. The system of claim 19, further comprising a medical device, wherein the processor is configured to control the medical device to withhold therapy delivery to the patient based on determining whether the detected tachyarrhythmia episode is a false positive detection attributable to electrical noise.

22. The system of claim 19, wherein the plurality of detected tachyarrhythmia events comprises a first detected tachyarrhythmia event and a second detected tachyarrhythmia event, and wherein the processor is configured to determine the variability in the plurality of cardiovascular pressure values by at least determining whether a first cardiovascular pressure value of the plurality of cardiovascular pressure values associated with the first detected tachyarrhythmia event and a second cardiovascular pressure value of the plurality of cardiovascular pressure values associated with the second detected tachyarrhythmia event are within a threshold range of each other.

23. The system of claim 19, wherein the processor is configured to determine the variability in the plurality of cardiovascular pressure values by at least determining whether the cardiovascular pressure associated with at least one detected tachyarrhythmia event of the plurality of detected tachyarrhythmia events varies by a threshold percentage compared to an average cardiovascular pressure value of cardiovascular pressures associated with at least two other detected tachyarrhythmia events of the plurality of detected tachyarrhythmia events.

24. The system of claim 19, wherein the processor is configured to determine the variability in the plurality of cardiovascular pressure values by at least determining whether at least one of a mean or a median value of the plurality of cardiovascular pressure values is within a threshold range of values.

25. The system of claim 19, wherein the processor is configured to determine the variability in the plurality of cardiovascular pressure values by at least determining at least one of a mean value or a median value of at least two cardiovascular pressure values of the plurality of cardiovascular pressure values, determining a plurality of absolute difference values, wherein each absolute difference value of the plurality of absolute difference values comprises an absolute difference between a respective cardiovascular pressure value of the plurality of cardiovascular pressure values and the at least one of the mean value or the median value of the at least two cardiovascular pressure values, and comparing each absolute difference value of the plurality of absolute difference values to a threshold value or a threshold range of values.

26. The system of claim 19, wherein the processor is configured to determine the variability in the plurality of cardiovascular pressure values by at least:

determining at least one of a mean value or a median value of at least two cardiovascular pressure values of the plurality of cardiovascular pressure values, determining a plurality of absolute difference values, wherein each absolute difference value of the plurality of absolute difference values comprises an absolute difference between a respective cardiovascular pressure value of the plurality of pressure values and the at least one of the mean value or the median value of the at least two cardiovascular pressure values, determining at least one of a mean value or a median value of the plurality of absolute difference values, and determining whether the at least one of the determined mean value or the determined median value of the plurality of absolute difference values is within a threshold range of the at least one of the mean value or the median value of the at least two cardiovascular pressure values of the plurality of cardiovascular pressure values.

27. The system of claim 19, wherein the processor is further configured to determine whether any of the plurality of detected tachyarrhythmia events comprises a short interval, generate a count of a number of the detected tachyarrhythmia events that comprise a short interval, and analyze the plurality of cardiovascular pressure values if the count is greater than or equal to a threshold value.

28. The system of claim 19, wherein the processor is further configured to compare each cardiovascular pressure value of the plurality of cardiovascular pressure values to a first threshold pressure value, generate a count of a number of cardiovascular pressure values of the plurality of cardiovascular pressure values that are less than or equal to the first threshold pressure value, and analyze the plurality of cardiovascular pressure values if the count is greater than or equal to a second threshold value.

29. The system of claim 19, further comprising a sensing module configured to generate a signal indicative of electrical activity within the heart, wherein the processor is configured to detect the tachyarrhythmia episode based on the signal generated by the sensing module.

30. The system of claim 19, wherein each of the cardiovascular pressure values of the plurality of cardiovascular pressure values comprises at least one of a pulse pressure value, an average pressure value, a systolic pressure value, or a diastolic pressure value.

31. The system of claim 19, wherein the tachyarrhythmia episode comprises at least one of a ventricular fibrillation episode, a ventricular tachycardia episode, a fast ventricular tachycardia episode or a non-sustained tachyarrhythmia episode.

32. The system claim 19, wherein the processor is configured to determine, based on the variability in the plurality of cardiovascular pressure values, whether the detected tachyarrhythmia episode is a false positive detection attributable to electrical noise by at least determining whether the variability in the plurality of cardiovascular pressure values is greater than a threshold variability value, determining that the detected tachyarrhythmia episode is the false positive detection attributable to electrical noise if the variability in the plurality of cardiovascular pressure values is greater than the threshold variability value, and determining that the detected tachyarrhythmia episode is not the false positive detection attributable to electrical noise if the variability in the plurality of cardiovascular pressure values is less than the threshold variability value.

33. A system comprising:
means for detecting a tachyarrhythmia episode of a heart of a patient, wherein the tachyarrhythmia episode comprises a plurality of detected tachyarrhythmia events;
means for analyzing a plurality of cardiovascular pressure values, each of the pressure values being associated with a respective one of the tachyarrhythmia events, wherein the means for analyzing the plurality of cardiovascular pressure values determines a variability in the plurality of cardiovascular pressure values; and
means for determining, based on the variability in the plurality of cardiovascular pressure values, whether the detected tachyarrhythmia episode is a false positive detection attributable to electrical noise.

34. A non-transitory computer-readable medium comprising instructions that cause a programmable processor to:
detect a tachyarrhythmia episode of a heart of a patient, wherein the tachyarrhythmia episode comprises a plurality of detected tachyarrhythmia events;
analyze a plurality of cardiovascular pressure values by at least determining a variability in the plurality of cardiovascular pressure values, each of the pressure values being associated with a respective one of the tachyarrhythmia events; and
determine, based on the variability in the plurality of cardiovascular pressure values, whether the detected tachyarrhythmia episode is a false positive detection attributable to electrical noise.

\* \* \* \* \*